(12) United States Patent
Katoh et al.

(10) Patent No.: US 7,381,200 B2
(45) Date of Patent: *Jun. 3, 2008

(54) INFUSION DEVICE

(75) Inventors: Osamu Katoh, 3-114-1102, Ohashidori, Toyohashi, Aichi-ken (JP); Manabu Shimogami, Seto (JP)

(73) Assignees: Asahi Intecc Co., Ltd., Aichi (JP); Osamu Katoh, Aichi (JP)

( * ) Notice: Subject to any disclaimer, the term of this patent is extended or adjusted under 35 U.S.C. 154(b) by 308 days.

This patent is subject to a terminal disclaimer.

(21) Appl. No.: 10/837,820

(22) Filed: May 3, 2004

(65) Prior Publication Data

US 2005/0004522 A1    Jan. 6, 2005

(30) Foreign Application Priority Data

May 6, 2003    (JP)    ............................. 2003-128125

(51) Int. Cl.
*A61M 5/178*    (2006.01)
(52) U.S. Cl. .............................. 604/164.13; 604/93.01; 604/164.01; 604/164.1; 604/264; 604/523
(58) Field of Classification Search ........... 604/164.01, 604/164.03, 164.06, 164.09, 164.13, 264, 604/510, 511, 522, 523, 528, 532, 506, 507, 604/93.01, 96.01, 164.1, 164.11, 170.01, 604/170.02, 170.03, 173, 272

See application file for complete search history.

(56) References Cited

U.S. PATENT DOCUMENTS

| RE31,873 E | 4/1985 | Howes |
|---|---|---|
| 4,578,061 A | 3/1986 | Lemelson |
| 4,601,701 A * | 7/1986 | Mueller, Jr. ................... 604/83 |
| 4,808,156 A * | 2/1989 | Dean ........................... 604/43 |

(Continued)

FOREIGN PATENT DOCUMENTS

EP    0 453 234 A1    10/1991

(Continued)

OTHER PUBLICATIONS

Katoh, et al., "Reagent Injecton Device," U.S. Appl. No. 10/793,351, filed Mar. 4, 2004.

*Primary Examiner*—Kevin C. Sirmons
*Assistant Examiner*—Laura C Schell
(74) *Attorney, Agent, or Firm*—Knobbe, Martens, Olson & Bear LLP

(57)    ABSTRACT

It is an object of the present invention to provide an infusion device that can be easily inserted into the body and that when inserted into a blood vessel reliably ensures the flow of blood. The infusion device is provided with a needle-shaped tube member having a sharp tip in any one lumen of the three lumens provided within a tubular member that can be inserted into the body in such a manner that it can move axially, an extrusion aperture provided in the tubular member through which the needle-shaped tube member is extruded, and a reagent supplier for supplying a predetermined reagent into the needle-shaped tube member. Additionally, recessed portions extending axially are formed in an outer circumferential surface of the tubular member in such a manner that the cross sectional shape perpendicular to the axial direction of the tubular member is a shape in which at least a portion of the outer circumference of an annular shape has been recessed radially inward.

26 Claims, 12 Drawing Sheets

U.S. PATENT DOCUMENTS

| | | | |
|---|---|---|---|
| 5,203,338 A * | 4/1993 | Jang | 600/463 |
| 5,209,741 A * | 5/1993 | Spaeth | 604/264 |
| 5,328,480 A * | 7/1994 | Melker et al. | 604/164.11 |
| 5,342,301 A * | 8/1994 | Saab | 604/103.13 |
| 5,354,279 A | 10/1994 | Höfling | |
| 5,419,777 A | 5/1995 | Höfling | |
| 5,464,395 A * | 11/1995 | Faxon et al. | 604/103.02 |
| 5,569,184 A * | 10/1996 | Crocker et al. | 604/509 |
| 5,702,384 A | 12/1997 | Umeyama et al. | |
| 5,797,869 A | 8/1998 | Martin et al. | |
| 5,916,194 A | 6/1999 | Jacobsen et al. | |
| 6,066,100 A * | 5/2000 | Willard et al. | 600/452 |
| 6,068,610 A | 5/2000 | Ellis et al. | |
| 6,135,976 A | 10/2000 | Tachibana et al. | |
| 6,217,554 B1 | 4/2001 | Green | |
| 6,248,122 B1 | 6/2001 | Klumb et al. | |
| 6,290,668 B1 * | 9/2001 | Gregory et al. | 604/22 |
| 6,302,870 B1 | 10/2001 | Jacobsen et al. | |
| 6,436,090 B1 * | 8/2002 | Sanchez et al. | 604/525 |
| 6,458,098 B1 | 10/2002 | Kanesaka | |
| 6,494,905 B1 | 12/2002 | Zedler et al. | |
| 6,524,302 B2 * | 2/2003 | Kelley | 604/523 |
| 6,884,258 B2 * | 4/2005 | Vardi et al. | 623/1.11 |
| 7,018,358 B2 * | 3/2006 | Joergensen et al. | 604/96.01 |
| 2001/0011180 A1 | 8/2001 | Fitzmaurice et al. | |
| 2001/0025134 A1 | 9/2001 | Bon et al. | |
| 2002/0055733 A1 | 5/2002 | Wilson | |
| 2002/0077591 A1 | 6/2002 | Happ et al. | |
| 2003/0171714 A1 | 9/2003 | Katoh et al. | |
| 2004/0176726 A1 | 9/2004 | Katoh et al. | |

FOREIGN PATENT DOCUMENTS

| | | |
|---|---|---|
| EP | 1070513 A1 | 7/2000 |
| EP | 1 342 486 A1 | 9/2003 |
| JP | 06-32655 | 5/1994 |
| JP | 2001-104487 | 4/2001 |
| JP | 2001-299927 | 10/2001 |
| JP | 2001-314514 | 11/2001 |
| JP | 2003-339874 | 12/2003 |
| WO | WO 99/44539 | 9/1999 |
| WO | WO 01/03762 A1 | 1/2001 |
| WO | WO 01/49357 A2 | 7/2001 |
| WO | WO 01/49357 A3 | 7/2001 |

* cited by examiner

INFUSION DEVICE

BACKGROUND OF THE INVENTION

1. Field of the Invention

The present invention generally relates to the structure of infusion devices for infusing a predetermined reagent to lesion portions, for example, in body tissue.

2. Description of the Related Art

Conventionally, medical devices such as catheters have been introduced into tubular organs in the body such as blood vessels, the alimentary canal, and the ureters to perform various treatments, tests, and procedures, for example. More recently, treatment and procedures in which infusion devices such as infusion catheters have been used to infuse a predetermined liquid medicine into lesion portions in body tissues have been performed (see JP 2001-104487A and JP 2001-299927A).

That is, as is well known in the art, such infusion catheters are constituted by a tubular catheter member into which a needle-shaped tube member made of a narrow tube capable of conducting a predetermined reagent and having a sharp tip portion is inserted and disposed in such a manner that it can move in the axial direction of the catheter member. The catheter member of such an infusion catheter is then inserted into a blood vessel and pushed through the vessel until reaching the site of a lesion in a body tissue, at which point the needle-shaped tube member is moved longitudinally. The needle-shaped tube member is thereby passed through a tip opening or an aperture portion provided in the tube wall of the catheter member and the needle portion of the tip of the needle-shaped tube member is extruded to the outside to penetrate a lesion portion of the body tissue, and in this state a predetermined reagent is infused into the lesion portion through the needle-shaped tube member.

One type of an infusion device, such as an infusion catheter, has a structure in which at least three lumens are provided inside the tubular member, these being a needle-shaped tube member lumen into which the needle-shaped tube member is movably inserted, a guide wire lumen into which a guide wire is inserted, and a balloon lumen for conducting fluid for expanding a balloon that is attached to the outside of the tubular member.

In infusion devices having such a structure, it is not possible to keep the cross sectional area of the tubular member perpendicular to its axial direction from becoming large. For that reason, when using such infusion devices there is the concern that depending on the site in the body to which it is to be inserted it may be difficult to insert the tubular member into the body, even if the tubular member has an annular profile perpendicular to its axis such that it can be inserted into the body as smoothly as possible. Moreover, there is also a concern that the flow of blood may be arrested when the tubular member has been inserted into a blood vessel, for example.

SUMMARY OF THE INVENTION

The present invention was arrived at in consideration of the foregoing matters, and it is an object thereof in an embodiment to provide an infusion device having a tubular member in which at least three lumens are provided, which can be easily inserted into the body and which allows the flow of blood through a blood vessel to be reliably secured even if the tubular member has been inserted into that blood vessel.

In order to solve the above problems, a primary aspect of an embodiment of the present invention is an infusion device having a tubular member, made of a tube member that can be inserted into a body, in which at least three lumens are provided, a needle-shaped tube member, made of a thin tube with a sharp tip, that is inserted into any one of the three lumens inside the tubular member such that it can be moved axially and whose sharp tip is extruded outside through an extrusion aperture provided in the tubular member so as to infuse a reagent (including at least one of natural or synthetic chemical components and biological elements such as cells, tissues, and biologically-derived or altered or natural components and any other components suitable for treatment), and a reagent supplier for supplying a predetermined reagent into the needle-shaped tube member, wherein when the tubular member has been inserted and placed within a body, the tip portion of the needle-shaped tube member is extruded from the extrusion aperture of the tubular member and penetrated into predetermined tissue within the body, such that a reagent that is supplied from the reagent supplier can be infused into that body tissue through the needle-shaped tube member, wherein a recessed portion extending in the axial direction is formed in an outer circumferential surface of the tubular member, such that a cross sectional shape of the tubular member perpendicular to the axial direction is a shape in which at least a portion of an outer circumference of an annular shape has been recessed radially inward.

In other words, with the infusion device according to an embodiment of the present invention, a recessed portion is formed in the outer circumferential surface of the tubular member such that the tubular member has a cross sectional shape perpendicular to its axis in which at least a portion of outer circumference of an annular shape has been recessed radially inward. Thus, compared to the tubular member of conventional devices, in which three or more lumens are formed therein and whose cross sectional shape perpendicular to its axis is annular, the cross sectional area in the direction perpendicular to the axis is reduced by an amount corresponding to the recessed portion that is formed. Thus, the geometrical moment of inertia is small and the tubular member is easily bent. Consequently, the tubular member easily follows areas within the body, such as blood vessels, into which it is inserted. Thus, the tubular member can be more smoothly inserted into the body than the tubular member of a conventional device.

Moreover, in the infusion device according to an embodiment of the present invention, the recessed portion formed in the outer circumferential surface of the tubular member extends in the axial direction of the tubular member. Thus, for example, when the tubular member has been inserted into a blood vessel, the presence of this recessed portion allows a gap through which blood can flow to be reliably formed between the outer circumferential surface of the tubular member and the inner wall surface of the blood vessel.

Consequently, with the infusion device according to an embodiment of the present invention described above, the tubular member can be easily inserted into the body, even it is internally provided with at least three or more lumens.

To solve the technical issues discussed above, a further aspect of an embodiment of the present invention is an infusion device having a tubular member, made of a tube member that can be inserted into a body, in which at least three lumens are provided, a needle-shaped tube member, made of a thin tube with a sharp tip, that is inserted into any one of the three lumens inside the tubular member such that it can be moved axially and whose sharp tip is extruded outside through an extrusion aperture provided in the tubular member so as to infuse a reagent, and a reagent supplier for supplying a predetermined reagent into the needle-shaped tube member, wherein when the tubular member has been inserted and placed within a body, the tip portion of the needle-shaped tube member is extruded from the extrusion aperture of the tubular member and penetrated into predetermined tissue within the body, such that a reagent that is supplied from the reagent supplier can be infused into that body tissue through the needle-shaped tube member, wherein the tubular member, in a cross-section perpendicular to its axial direction, has an outer circumferential surface made of three convex curved corner portions each positioned corresponding to apexes of a triangle that is formed having the center points of any three lumens of the at least three lumens serving as its apexes, and three lateral surfaces that are curved surfaces or flat surfaces each positioned corresponding to the bases of this triangle and connecting convex curved corner portions that are adjacent.

That is, in the infusion device according to an embodiment of the present invention, the tubular member has an outer circumferential surface formed only by three convex curved corner portions and three lateral surfaces, which are either curved surfaces or flat surfaces. Thus, with this infusion device, the cross sectional shape perpendicular to the axial direction of the tubular member is substantially triangular, having three rounded corner portions and three bases constituted by straight or curved lines. The cross sectional area perpendicular to the axial direction of the tubular member can therefore be made sufficiently smaller than the cross sectional area of the tubular member of a conventional device, in which three or more lumens are provided inside the tubular member and its cross sectional shape perpendicular to its axis is annular. Thus, the geometrical moment of inertia is small and the tubular member is easily bent. The tubular member therefore easily follows areas within the body, such as blood vessels, into which it is inserted. Consequently, the tubular member can be more smoothly inserted into the body than the tubular member of a conventional device.

Moreover, in the infusion device according to an embodiment of the present invention, the tubular member has three lateral surfaces which are curved or flat surfaces and which provide the three bases of the cross section shape in the direction perpendicular to the axis that give a substantially triangular shape. Thus, for example, when the tubular member has been inserted into a blood vessel, a gap that allows blood to flow therethrough can be reliably formed between these three lateral surfaces and the inner wall surface of the blood vessel.

Consequently, the infusion device according to an embodiment of the present invention described above can be easily inserted into the body even though at least three lumens are provided within it. It also allows the flow of blood within a blood vessel into which it has been inserted to be reliably secured.

It should be noted that in one preferable configuration of the foregoing infusion device according to an embodiment of the present invention, a maximum width in the direction of extrusion of the needle-shaped tube member from the extrusion aperture in a cross section of the needle-shaped tube member taken perpendicular to the axial direction is smaller than a maximum width in a direction perpendicular to the direction of extrusion of the needle-shaped tube member in that cross section.

In an infusion device having this configuration, the tubular member can be easily curved in the direction in which the needle-shaped tube member is extruded from the extrusion aperture. Thus, when the tubular member has been inserted into the body, it is easily curved along contours within the body, making insertion of the tubular member into the body easy. Further, the section of the tubular member with a large width, that is, the section whose area is large, is brought into close contact with a section in the body due to the reaction force when the needle-shaped tube member is extruded from the extrusion opening and penetrates body tissue, and thus the tubular member can reliably receive and stop the reaction force resulting from this penetration by the needle-shaped tube member. The needle-shaped tube member can therefore be easily and reliably advanced into body tissue.

In another favorable embodiment of the infusion device according to an embodiment of the present invention, the front end portion of the needle-shaped tube member in the direction of insertion into the body is smaller in a cross section of the tubular member taken perpendicular to the axial direction than in a section other than the front end portion of the tubular member.

In an infusion device having this configuration, the front end portion of the tubular member, whose sectional area perpendicular to the axial direction has been made small, can be provided with flexibility. Thus, the tubular member can be safely inserted into the body without damaging inner wall surfaces within the body. Furthermore, reducing the cross sectional area of the tubular member in a section perpendicular to the axial direction in the front end portion has the added benefit that when the tubular member has been inserted into a blood vessel the flow of blood through that blood vessel can be favorably secured.

In yet another preferable embodiment of the infusion device according to an embodiment of the present invention, the at least three lumens provided in the tubular member include a needle-shaped tube member lumen into which the needle-shaped tube member is inserted, a first guide wire lumen into which a first guide wire that is extended from a tip of the tubular member is inserted such that it can be moved in the axial direction of the tubular member, and a balloon lumen for supplying fluid into a balloon that can expand and contract and that is attached to an outside portion of the tubular member.

With an infusion device having the foregoing configuration, even if the tubular member is inserted up to a predetermined site within a blood vessel and the balloon is expanded at that site, for example, the flow of blood can be satisfactorily secured.

In a yet further preferable embodiment of the infusion device according to an embodiment of the present invention, the at least three lumens provided in the tubular member include a needle-shaped tube member lumen into which the needle-shaped tube member is inserted, a first guide wire lumen into which a first guide wire that is extended from a tip of the tubular member is inserted such that it can be moved in the axial direction of the tubular member, and a second guide wire lumen into which a second guide wire that is extended in a direction intersecting the first guide wire is inserted such that it can be moved in the axial direction of the tubular member, and a plane that includes the direction vector in which the first guide wire is extended and a direction vector in which the second guide wire is extended is substantially perpendicular to the direction in which the extrusion aperture is provided.

In an infusion device having such a configuration, the plane that includes the direction vector in which the first guide wire is extended and the direction vector in which the second guide wire is extended is substantially approximate to the surface of the body tissue that is to be penetrated. Also, the plane including direction of extrusion of the needle-shaped tube member that is extruded from the extrusion aperture of the tubular member and the axial direction of the tubular member is substantially perpendicular to the plane including the direction vectors for the first and second guide wires. The needle-shaped tube member can therefore be extruded from the extrusion aperture of the tubular member in a direction that is substantially perpendicular to the surface of the body tissue to be penetrated. Thus, the needle portion can be penetrated into a desired location of a lesion portion of body tissue.

Furthermore, in this infusion device, most of the reaction force that is generated as the needle-shaped tube member is advanced into body tissue when the needle-shaped tube member is penetrated into the body tissue is applied in a direction substantially perpendicular to the surface of the body tissue, that is, a direction substantially perpendicular to the plane including the direction vector in which the first guide wire is extended and the direction vector in which the second guide wire is extended and which is opposite to the direction in which the needle-shaped tube member is advanced. Thus, this reaction force is divided between the first guide wire and the second guide wire and is thereby sufficiently and reliably stopped. As a result, the needle-shaped tube member can be very smoothly and reliably advanced into body tissue.

Consequently, with the infusion device having the foregoing configuration, the needle-shaped tube member can be reliably penetrated into a predetermined site of body tissue up to a desired depth, even if the body tissue that penetrates is relatively hard. As a result, a greater effect with treatment or procedures in which a predetermined liquid medicine is infused into a lesion portion can be attained.

It should be noted that strictly speaking, "substantially perpendicular" here is used taking into account that there may be cases in which the needle-shaped tube member is not extruded perpendicular to a portion of the surface of the body tissue due to the fact that in practice, the surface of body tissue has a complex shape. In other words, in an embodiment of the present invention, the state of the plane including the direction vector in which the first guide wire is extended and the direction vector in which the second guide wire is extended being substantially perpendicular to the direction in which the extrusion aperture is provided also includes the state of that plane intersecting the direction in which the extrusion aperture is provided at an angle that is approximate to a right angle.

Further, in the infusion device, if the first guide wire and the second guide wire are inserted into the first guide wire lumen and the second guide wire lumen, respectively, then, preferably, the first guide wire lumen and the second guide wire lumen are provided within the tubular member such that the plane including the central axis of the first guide wire lumen and the central axis of the second guide wire lumen is perpendicular to the direction in which the extrusion aperture is provided.

In an infusion device having such a configuration, the needle-shaped tube member can be more reliably extruded from the extrusion aperture of the tubular member in a direction that is substantially perpendicular to the plane including the direction of extension of the first guide wire and the direction of extension of the second guide wire. Thus, most of the reaction force that is generated when the needle portion is advanced into body tissue is more adequately and reliably received and stopped by the first guide wire and the second guide wire. As a result, the needle portion can be even more smoothly and reliably advanced into body tissue.

Further, in an infusion device having a structure in which the first and the second guide wires are inserted into first and second guide wire lumens as described above, it is preferable that the first guide wire lumen and the second guide wire lumen are provided within the tubular member such that they are disposed on either side of the needle-shaped tube member and sandwich it between them, and that their central axes are located on the same plane as the central axis of the needle-shaped tube member lumen.

By adopting such a configuration, the distance between the first and the second guide wire lumens can be made as large as possible, and the distance between the first and the second guide wires that are extended outward from the first and the second guide wire lumens can also be made large. As a result, most of the reaction force that is generated when the needle portion is advanced into body tissue is more adequately and reliably received by the first guide wire and the second guide wire.

Yet further, in the infusion device according to an embodiment of the present invention, if a structure in which the first guide wire and the second guide wire are inserted into the first guide wire lumen and the second guide wire lumen is adopted, then it is preferable that a balloon that can be expanded and contracted is attached to the outside of the tubular member, and that a balloon lumen for conducting for expanding the balloon is further provided within the tubular member.

If such a configuration is adopted, then by expanding the balloon the tubular member can be easily fastened to a predetermined site in the body. This allows the needle-shaped tube member to more reliably penetrate a predetermined location in body tissue up to a desired depth.

Also, if a balloon and a balloon lumen are provided outside and inside the tubular member as described above, then the four lumens are preferably provided within the tubular member such that the plane that includes the central axes of the first guide wire lumen and the second guide wire lumen and the plane that includes the central axes of the needle-shaped tube member lumen and the balloon lumen are positioned perpendicular to one another. The four lumens are thus disposed well balanced within the tubular member. As a result, tasks in which an infusion device having such a tubular member is employed can be carried out more smoothly.

Further, in the infusion device according to an embodiment of the present invention, if a structure in which a balloon and a balloon lumen are provided outside and inside the tubular member is adopted, then it is preferable that the balloon lumen and the needle-shaped tube member lumen are provided within the tubular member such that the center of the extrusion aperture is located on a plane that includes their central axes. By doing this, the balloon lumen is disposed with greater balance within the tubular member. Thus, tasks in which the infusion device is employed can be carried out more smoothly.

In another embodiment, the present invention provides an infusion device, comprising: (i) a tubular member, made of a tube member that can be inserted into a body, in which at least three lumens are provided; (ii) a needle-shaped tube member, made of a thin tube with a sharp tip, that is inserted into one of the three lumens inside the tubular member such that it can be moved axially, and whose tip is extruded outside through an extrusion aperture provided in the tubular member so as to infuse liquid medicine; and (iii) a recessed portion formed in an outer circumferential surface of the tubular member and extending in the axial direction thereof, such that a cross sectional shape of the tubular member perpendicular to the axial direction is a shape in which at least a portion of the outer circumference of an annular cross section has been recessed radially inward.

Further, in another embodiment, the present invention provides an infusion device, comprising: (i) a tubular member configured to be inserted into a body, having at least three lumens extending in its axial direction and an extrusion aperture provided on a side wall of the tubular member, one of said lumens leading to the extrusion aperture, said tubular member having a cross section perpendicular to the axial direction; and (ii) a needle-shaped tube member with a sharp tip, that is inserted into said one of the lumens and is movable axially, said tip being extruded outside through the extrusion aperture for infusing a reagent, wherein the cross section has an outer periphery formed from an imaginary circle by moving inward a portion of the circle corresponding to at least one side of an imaginary polygon, where the imaginary polygon having apexes is defined by the center points of the lumens and has sides each connecting two adjacent apexes, and the imaginary circle has a smallest diameter for fitting the cross section inside, wherein the imaginary polygon is fitted therein. The outer periphery may be composed of concave, convex, and/or straight lines. Any combination can be adopted in view of flexibility, rigidity, and a function of allowing for blood flow. The lumens need to be formed with a material having a thickness for sufficient mechanical strength, whereas a portion apart from the lumens can be thin. The above embodiment further includes, but is not limited to, the following additional embodiments:

The at least three lumens may be three lumens at the front end portion and four lumens at a rear end portion opposite to the front end portion.

The four lumens may include a first guide wire lumen into which a first guide wire that is extended from a tip of the tubular member is inserted and movable axially, and a second guide wire lumen into which a second guide wire that is extended from an opening provided on a side wall in a different direction from the first guide wire is inserted an movable axially, wherein the second guide wire lumen ends at the opening, and the tubular member has a smaller cross sectional area perpendicular to the axial direction between the tip and the opening than a cross sectional area perpendicular to the axial direction between opening and the rear end.

The first guide wire extending from the tip and the second guide wire extending may from the opening form a plane perpendicular to the direction of extrusion of the needle-shaped tube member from the extrusion aperture.

The cross sectional area between the tip and the opening may be such that the closer the distance to the tip, the smaller the area becomes.

The infusion device may further comprise a balloon attached to an outside portion of the tubular member, wherein one of the at least three lumens is a balloon lumen for conducting fluid for expanding the balloon, wherein a plane that includes the central axes of the first guide wire lumen and the second guide wire lumen, and a plane that includes the central axes of the needle-shaped tube member lumen and the balloon lumen, are disposed perpendicular to one another.

A center of the extrusion aperture may be disposed on the plane that includes the central axes of the needle-shaped tube member lumen and the balloon lumen.

In the present invention, any element used in an embodiment can interchangeably be used in another embodiment as long as it is feasible.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DETAILED DESCRIPTION OF THE PREFERRED EMBODIMENT

To make the present invention more readily apparent, configurations of infusion devices according to embodiments of the present invention are described in detail below with reference to the drawings. However, the present invention should not be limited to these embodiments.

Figure 1:
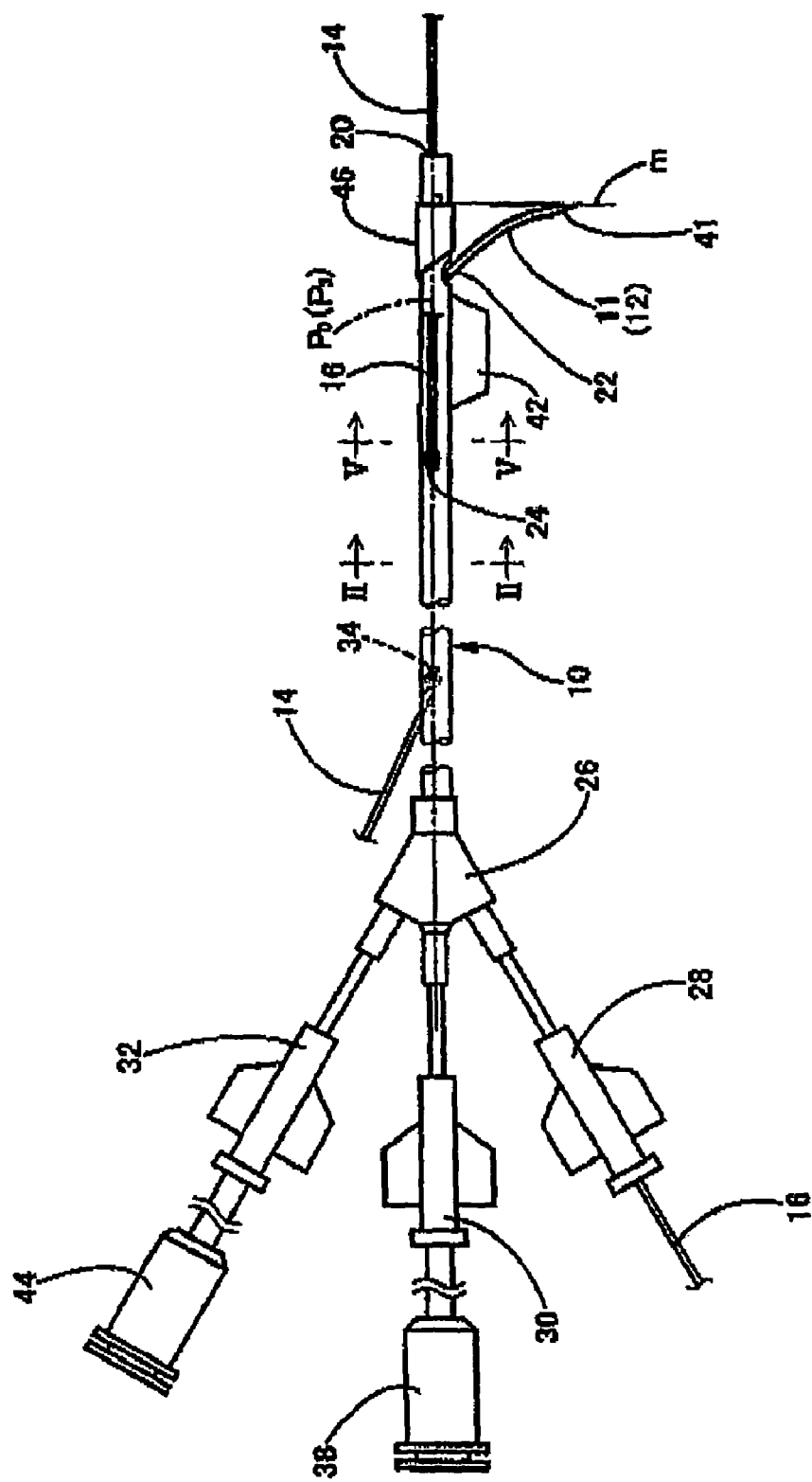
FIG. 1 is a plan view that schematically shows an example of a reagent infusion catheter having a structure according to the present invention.
Figure 2:
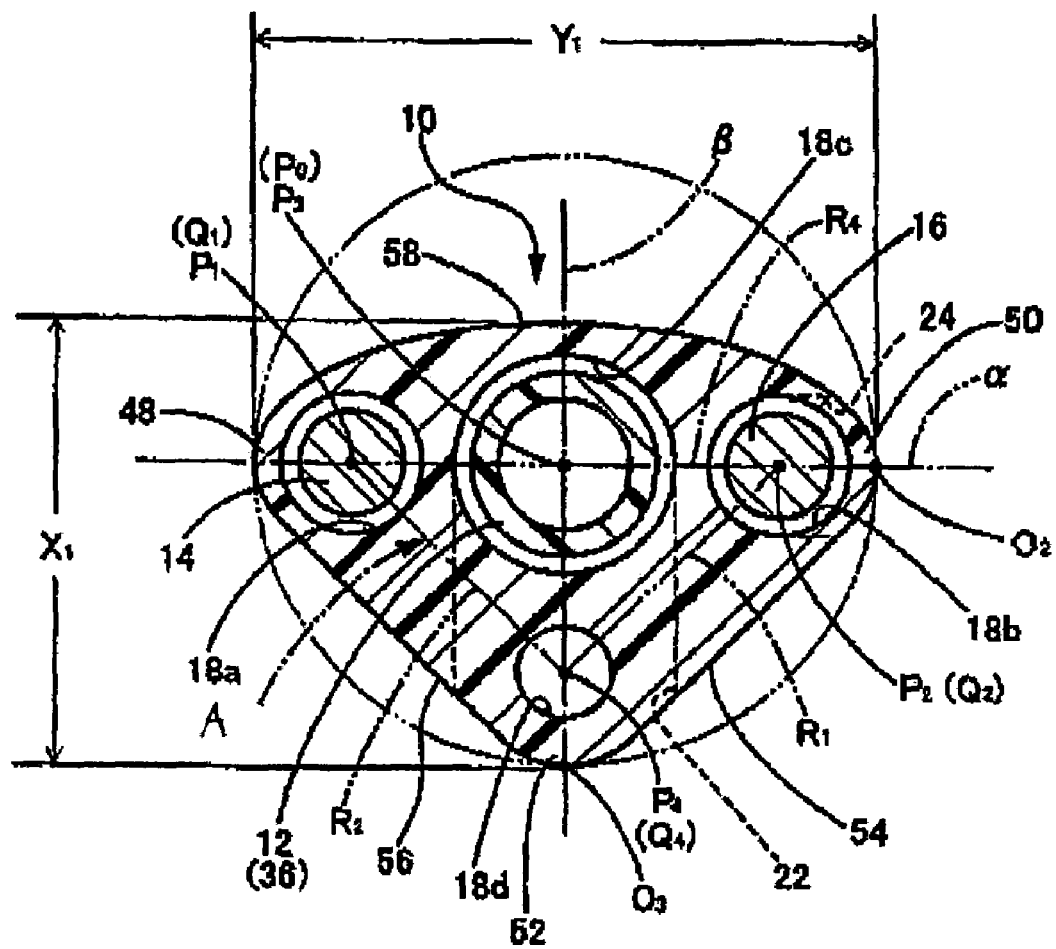
FIG. 2 is a diagram showing a magnification of a section taken along line II-II in FIG. 1.

First, FIG. 1 and FIG. 2 schematically show a front view and a vertical section, respectively, of an infusion catheter that is employed to infuse a reagent to a lesion portion in cardiac muscle as one embodiment of the infusion device having the structure according to the present invention. In FIGS. 1 and 2, reference numeral 10 denotes a catheter member made of an elongate tubular member serving as the tubular member, into which a needle-shaped tube member 12 whose tip portion is a sharp needle portion 11, a first guide wire 14, and a second guide wire 16 each are inserted in such a manner as to allow movement thereof in the axial direction.

More specifically, the catheter member 10 has a length and a thickness over its entire length that permits it to be inserted into a blood vessel extending from the femoral area or the wrist area of a human body to the heart. Further, the catheter member 10 includes a pliable stainless steel wire buried sandwiched between cylindrical inner and outer layers each made of a predetermined resin layer. Thus, the catheter member 10 is provided with a good balance of sufficient hardness and flexibility that allows it to be smoothly inserted into winding blood vessels. It should be noted that there are no particular limitations regarding the materials providing such a catheter member 10, and in addition to the above-mentioned materials, it is also possible to suitably adopt materials having a desired elasticity, including synthetic resin materials such as polyamide, super elastic metal alloy materials such as Ni—Ti alloys, and metallic materials such as stainless steel.

Additionally, first through fourth lumens 18a to 18d extending contiguously in the lengthwise direction are provided independent of one another within the catheter member 10.

Of the four lumens 18a to 18d, the first and second lumens 18a and 18b have an identical diameter that is smaller than that of the third lumen 18c, whose lumen diameter is the largest, and larger than that of the fourth lumen 18d, whose lumen diameter is the smallest, and both are disposed such that the central axis $P_0$ of the catheter member 10 is positioned on a plane α (indicated by the long-short dashed line in FIG. 2) that includes their central axes $P_1$ and $P_2$. The third lumen 18c is disposed such that its central axis $P_3$ matches the central axis $P_0$ of the catheter member 10, and is centrally positioned between the first lumen 18a and the second lumen 18b. Furthermore, the fourth lumen 18d is disposed at a position where a plane β including its central axis $P_4$ and the central axis $P_3$ of the third lumen 18c (shown by a long-short dashed line in FIG. 2) is perpendicular to the plane α that includes the central axes $P_1$ and $P_2$ of the first lumen 18a and the second lumen 18b.

The catheter member 10 including the four lumens 18a to 18d internally also has a tip opening 20 that opens in the axial direction in the tip of the end portion on the front side in the direction that the catheter member 10 is inserted into a blood vessel (the right side in FIG. 1). Moreover, an extrusion aperture 22 passing through the catheter wall and opening laterally is provided at a site slightly rearward of the tip in the front end portion of the catheter member 10. The catheter member 10 is further provided with a lateral aperture 24 that passes through the catheter wall at a site slightly more rearward the site where the extrusion aperture 22 is formed in the front end portion of the catheter member 10.

As is clear from FIG. 2 and FIG. 3, which is discussed later, of the three aperture portions 20, 22, and 24 that are provided in the front end portion of the catheter member 10, the tip opening 20 and the lateral aperture 24 are each disposed such that their center points $O_1$ and $O_2$ are positioned on the plane α that includes the central axes $P_1$ and $P_2$ of the first lumen 18a and the second lumen 18b. On the other hand, the extrusion aperture 22 is disposed such that its center point $O_3$ is positioned on the plane β, which includes the central axis $P_0$ of the catheter member 10 and is perpendicular to the plane α. Thus, here the lateral aperture 24 is provided in the direction perpendicular to the direction in which the tip opening 20 and the extrusion aperture 22 are provided.

In this manner, the tip opening 20 provided in the front end portion of the catheter member 10 is in communication with the first lumen 18a. Moreover, the lateral aperture 24 is in communication with the second lumen 18b, and the extrusion aperture 22 is in communication with the third lumen 18c. Thus, at the front end portion of the catheter member 10 the first lumen 18a opens toward the front side in the axial direction (to the right in FIG. 1) via the tip opening 20. Also, the second lumen 18b opens laterally at a right angle to the direction in which the first lumen 18a is provided (in FIG. 1, the direction perpendicular to the paper plane) via the lateral aperture 24. Further, the third lumen 18c opens in the direction perpendicular to both the direction in which the first lumen 18a is open or the direction in which the second lumen 18b is open (downward in FIG. 1) via the extrusion aperture 22.

On the other hand, three connectors 28, 30, and 32 are attached to the end portion on the rear side in which the catheter member 10 is inserted into a blood vessel (the left side in FIG. 1) via a branching socket 26 that branches the catheter member 10 into three. Additionally, an insertion opening 34 that passes through the wall of the catheter member 10 and is provided in the direction opposite the direction in which the lateral aperture 24 is provided with respect to in the radial direction of the catheter member 10 is formed a predetermined distance in front of the site where the branching socket 26 is provided in the rear end portion of the catheter member 10.

Then, the three connectors 28 to 32 are each brought into communication with the second through fourth lumens 18b to 18d, respectively, provided within the catheter member 10. Also, the insertion aperture 34 is brought into communication with the first lumen 18a. Thus, in the rear end portion of the catheter member 10 in the direction in which the catheter member 10 is inserted into a blood vessel, the first lumen 18a opens outward via the insertion aperture 34, whereas the second, third, and fourth lumens 18b to 18d open outward through the openings of the three connectors 28 to 32.

Next, as discussed above, here the needle-shaped tube member 12 and the first and second guide wires 14 and 16 are each inserted into the catheter member 10 such that they can move axially. The first guide wire 14 is inserted into the first lumen 18a provided within the catheter member 10 via the insertion aperture 34, which is provided in the wall of the rear end portion of the catheter member 10. On the other hand, the second guide wire 16 is inserted into the second lumen 18b provided within the catheter member 10 via the opening (rear end opening) of the connector 28, which is attached to the rear end portion of the catheter member 10.

Further, the needle-shaped tube member 12 is inserted into the third lumen 18c provided within the catheter member 10 via the opening of the connector 30, which is attached to the rear end portion of the catheter member 10.

Figure 3:
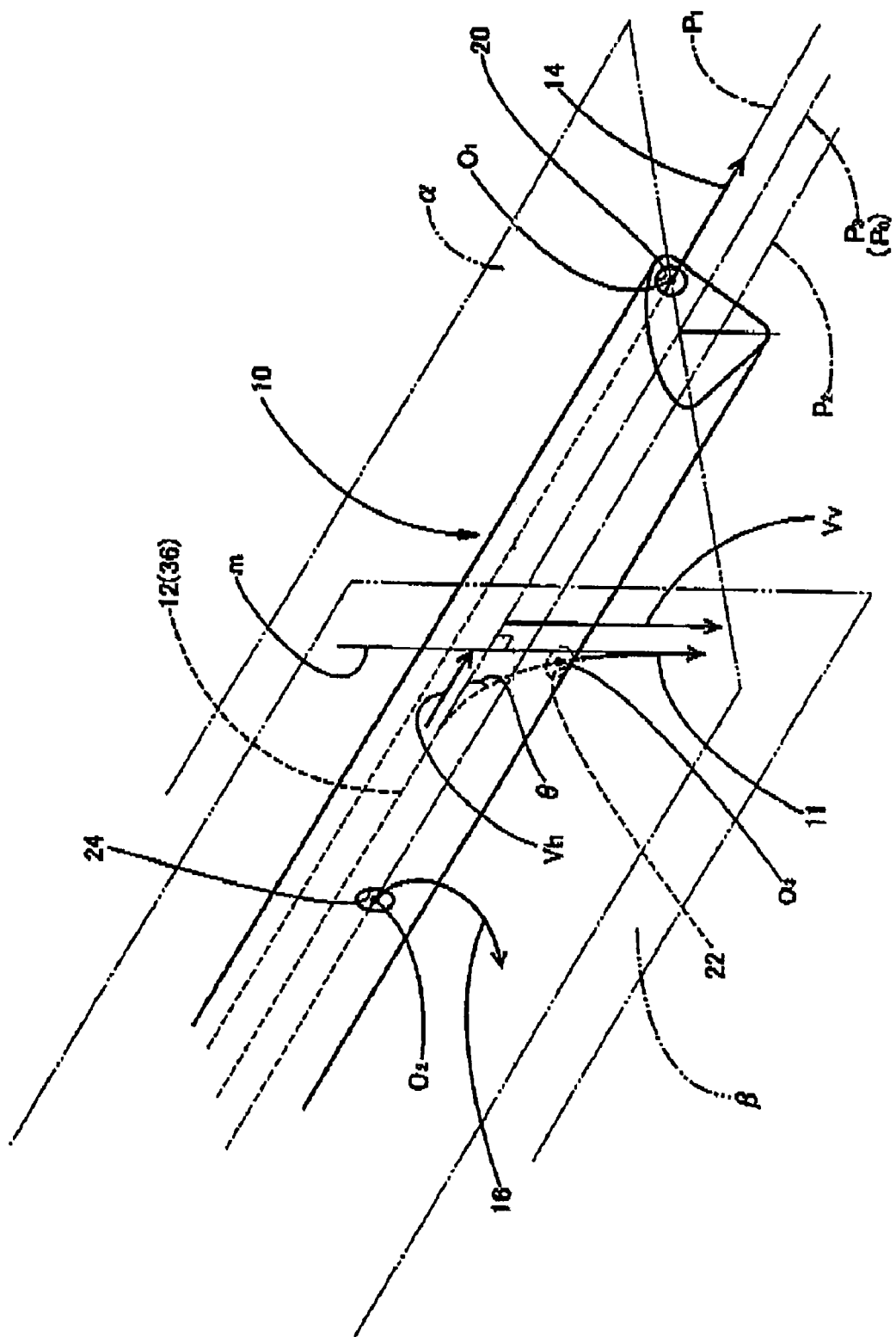
FIG. 3 is a diagram that schematically represents the structure of the reagent infusion catheter, showing the positions of the central axes of a needle-shaped tube member and first and second guide wires that have been inserted into the catheter member of the infusion catheter shown in FIG. 1.

Consequently, as is clear from FIG. 1 and FIG. 3, which illustrates the position of the central axes of the needle-shaped tube member 12 and the guide wires 14 and 16, by moving the first guide wire 14 axially forward within the first lumen 18a it can be extended axially forward from inside the first lumen 18a on the plane α through the tip opening 20 of the front end portion of the catheter member 10. Also, by moving the second guide wire 16 axially forward within the second lumen 18b it can be extended laterally with respect to the axial direction from inside the second lumen 18b on the plane α through the lateral aperture 24 of the front end portion of the catheter member 10. Furthermore, by moving the needle-shaped tube member 12 axially forward within the third lumen 18c, the needle portion 11 of its tip can be extruded outward on the plane β, which perpendicularly intersects the plane α, through the extrusion aperture 22 from inside the third lumen 18c in the direction perpendicular to both the direction in which the first guide wire 14 is extended and the direction in which the second guide wire 16 is extended. It can be understood from this description that in the present embodiment the first lumen 18a and the second lumen 18b constitute the first guide wire lumen and the second guide wire lumen, respectively, and the third lumen 18c constitutes the needle-shaped tube member lumen.

Figure 4:
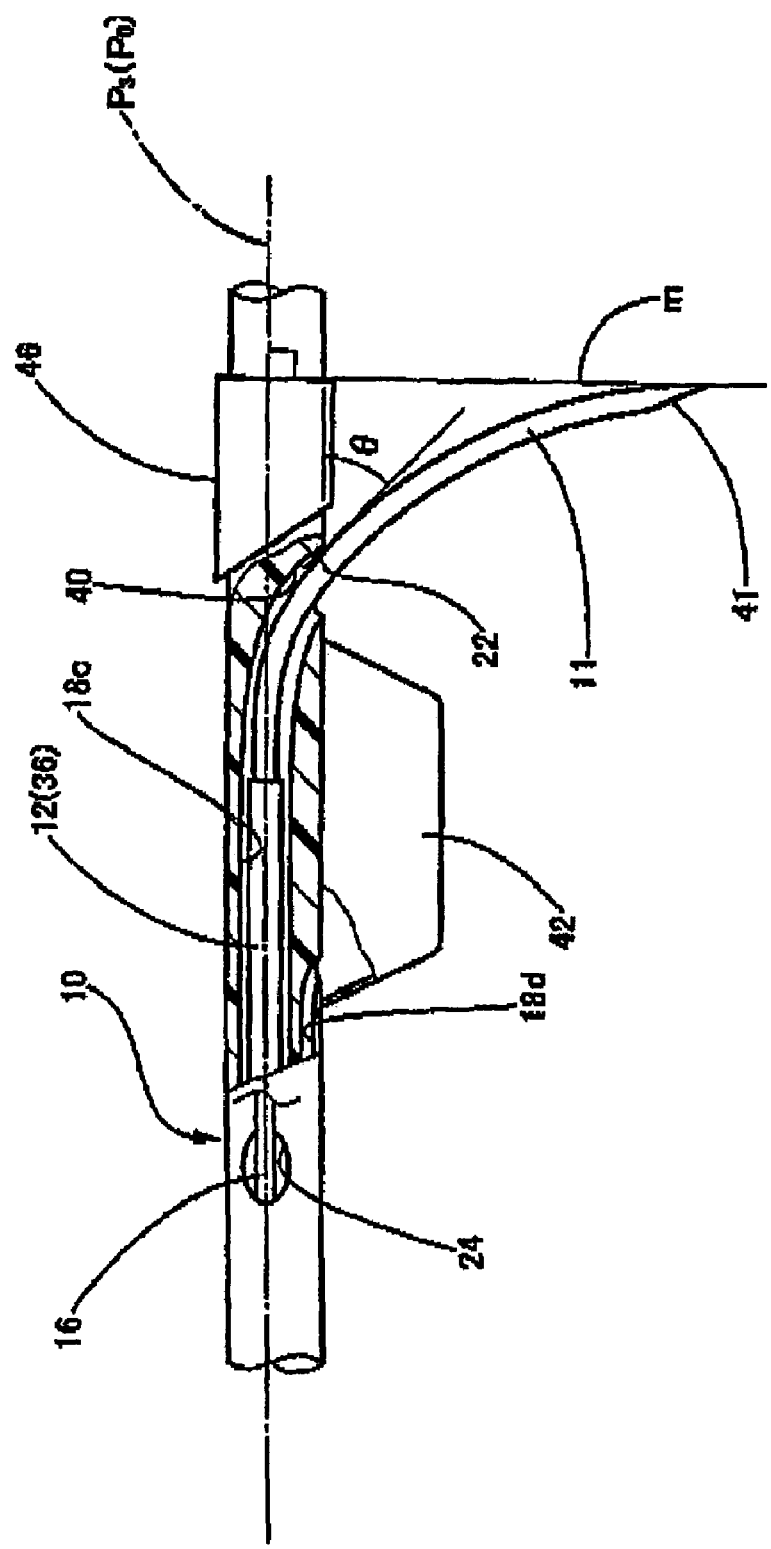
FIG. 4 is a diagram showing a partial magnification of the infusion catheter shown in FIG. 1, and includes partially notched representations.

As can be understood from FIGS. 2 to 4, the needle-shaped tube member 12 that is inserted into the third lumen 18c is made of a narrow tube that is overall pliable. Also, the needle-shaped tube member 12, excluding the needle portion 11 provided in its tip, is constituted by a reagent conduction duct portion 36 made of a narrow tube that is longer than the catheter member 10 and that has a diameter of about 0.4 mm. That is, the needle-shaped tube member 12 is a single unit constituted by the needle portion 11 and the reagent conduction duct portion 36.

The reagent conduction duct portion 36 of the needle-shaped tube member 12 is for example made of a pliable synthetic resin material such as polytetrafluoroethylene or polyimide. On the other hand, the needle portion 11 is made of an elastic material such as a super elastic alloy material such as an Ni—Ti alloy or a metallic material such as stainless steel. The reagent conduction duct portion 36 of the needle-shaped tube member 12 is connected to a syringe 38 serving as a reagent supply device for supplying a predetermined reagent that is attached via the connector 30.

Thus, the needle-shaped tube member 12 is provided with sufficient flexibility and elasticity and can be smoothly inserted into and moved axially within the third lumen 18c of the catheter member 10 which has been inserted into and follows curved and winding blood vessels. Also, by moving the needle-shaped tube member 12 axially forward within the third lumen 18c, the needle portion 11 can be extruded to the outside through the extrusion aperture 22 of the catheter member 10 made to penetrate cardiac muscle. Moreover, a reagent, including cells or growth factors such as bFGF (basic Fibroblast Growth Factor), VEGF (Vascular Endothelial Growth Factor), HGF (Hepatocyte Growth Factor) or the like, for regenerating nearly or substantially dead cardiac muscle can be introduced into the reagent conduction duct portion 36 through the syringe 38 and ejected to the outside from the opening of the needle portion 11 of its tip.

As shown in FIG. 4, here the inner circumferential surface of the front end portion of the third lumen 18c that includes the opening periphery portion of the extrusion aperture 22 serves as a guide surface 40 that is constituted by a convex curved surface that curves axially forward in the direction of the opening of the extrusion aperture 22. The needle portion 11 of the needle-shaped tube member 12 also has a curved shape that corresponds to the curved shape of the guide surface 40. Thus, the needle portion 11 is slid along the guide surface 40 in conjunction with axially forward movement of the needle-shaped tube member 12, and due to the guide surface 40, is smoothly guided toward the extrusion aperture 22.

It should be noted that the curved shapes of the guide surface 40 and the needle portion 11 can be suitably determined by taking account of the rigidity of the needle portion 11, for example. Also, there are no particular limitations regarding the size of the radius of curvature of the sites of curvature in the guide surface 40 or the needle portion 11. However, it is preferable that the extrusion angle θ at the point of contact between the guide surface 40 and the needle portion 11 is 45° or larger where the curved shape of the guide surface 40 and the curved shape of the needle portion 11 are combined while the needle portion 11 is extruded from the extrusion aperture 22.

Thus, as shown in FIG. 4, when the needle portion 11 has been adequately extruded from the extrusion aperture 22, the tip area of the needle portion 11 approaches the extrusion aperture 22 side so that it is easy to identify the position of the needle portion 11 when extruded. Moreover, it is possible to position the needle portion 11 such that the tangent m of the needle portion 11 is perpendicular to the central axis $P_0$ of the catheter member 10 and the central axis $P_3$ of the third lumen 18c into which the needle-shaped tube member 12 is inserted, at a position closer to the extrusion aperture 22. Consequently, the component force of the direction in which the needle-shaped tube member 12 is advanced toward cardiac muscle (of the two vectors Vv and Vh shown in FIG. 3, the size of the vector Vv perpendicular to the central axis $P_3$ of the third lumen 18c) becomes large, and thus the needle-shaped tube member 12 can be more smoothly advanced into cardiac muscle.

Additionally, here the tip surface of the needle portion 11, that is, an open end surface 41 in the opening of the needle portion 11, is provided as a slanted surface that slants in the direction in which the extrusion aperture 22 is provided toward the front of the catheter member 10, that is, as shown in FIG. 4, it is provided as a slanted surface in which the lower side of the needle portion 11 is slanted.

A balloon 42 is provided between the areas where the extrusion aperture 22 and the lateral aperture 24 are formed in the front end portion of the catheter member 10. The balloon 42 is made of a pliable synthetic resin material and has a well-known structure in which a fluid such as physiological saline solution can be introduced therein to expand the balloon 42 in the direction in which the extrusion aperture 22 is provided, and by discharging this fluid, the balloon can be shrunk from this expanded state. The fourth lumen 18d opens toward the interior of the balloon 42. Also, as is clear from FIG. 1, a syringe 44 serving as a fluid supply device that supplies fluid for expanding the balloon 42 is connected to the connector 32, which is attached to the rear end portion of the catheter member 10 and in communication with fourth lumen 18d. It is clear from this description that in the present embodiment, the fourth lumen 18d constitutes the balloon lumen.

It should be noted that in FIGS. 1 and 4 that the reference numeral 46 denotes a marker tube that has been formed using a radiopaque material such as gold, platinum, a platinum-rhodium alloy, or the like. An open end face on one side in the axial direction of the marker tube 46 is a slanted face, and a longest site and a shortest site of axial length are formed in its cylindrical wall portion. The marker tube 46 is fastened as a sleeve to the catheter member 10, with either the longest site or the shortest site of its cylindrical wall portion corresponding to the position of the extrusion aperture 22 formed in the catheter member 10. The tip of the marker tube 46 substantially matches the tangent m of the needle-shaped tube member 12 (needle portion 11) when the needle-shaped tube member 12 has been extruded. Thus, when the catheter member 10 has been inserted into a blood vessel, the position of the extrusion aperture 22 and the position of the tip of the needle-shaped tube member 12 can be easily ascertained by passing X-rays through the tip portion, the longest site, and the shortest site of the cylindrical wall portion of the marker tube 46. It should be noted that in the present embodiment, the shortest site of the cylindrical wall portion of the marker tube 46 is positioned on the extrusion aperture 22 side as shown in FIG. 4. It is also possible to attach the marker tube 46 by burying it in the catheter member 10.

Incidentally, with the infusion catheter of the present embodiment having the above configuration, in particular the catheter member 10 internally provided with the four lumens 18a to 18d, these being the first through third lumens 18a to 18c in which the first and second guide wires 14 and 16 and the needle-shaped tube member 12 are inserted and the fourth lumen 18d for introducing fluid for expanding the balloon 42, has a unique construction that is not found in conventional devices.

Figure 5:
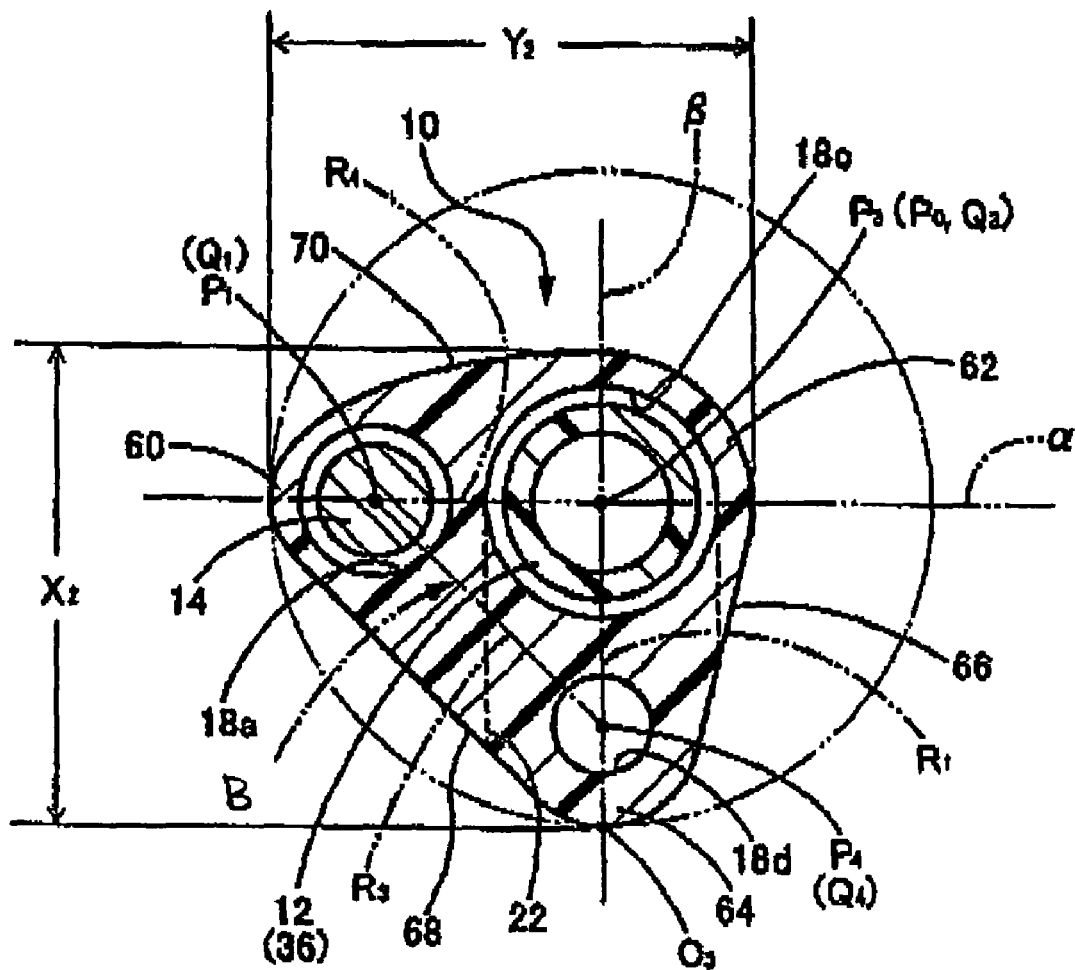
FIG. 5 is a diagram showing a magnification of a section taken along line V-V in FIG. 1.

That is, FIG. 2 shows the cross sectional shape perpendicular to the axial direction at the rear section of the catheter member 10 inside which the first through fourth lumens 18a to 18d are provided. Also, FIG. 5 shows the cross sectional shape (transverse cross section) perpendicular to the axial direction at the front section of the catheter member 10 in which the first lumen 18a and the third and fourth lumens 18c and 18d are provided. These two cross sectional shapes are substantially triangular shapes that are different in size.

More specifically, as shown in FIG. 2, a rear section of the catheter member 10, or in other words, a site more rearward than the site where the lateral aperture 24 is formed in the catheter member 10, in transverse cross section has three convex curved corner portions 48, 50, and 52 respectively positioned corresponding to the apexes $Q_1$, $Q_2$, and $Q_4$ of a triangle A (shown by a long-short dashed line in FIG. 2) that has been formed with the central axes (center points) $P_1$, $P_2$, and $P_4$ of the first lumen 18a, the second lumen 18b, and the fourth lumen 18d serving as its apexes, and has three lateral faces 54, 56, and 58 positioned corresponding to the three bases $R_1$, $R_2$, and $R_4$ of this triangle A. Of the three convex curved corner portions 48, 50, and 52, adjacent portions are connected by the three lateral faces 54, 56, and 58.

Thus in the infusion catheter of the present embodiment, the outer circumferential surface shape of the rear section of the catheter member 10 is substantially triangular with rounded corner portions. That is, the transverse profile of the rear section of the catheter member 10 (the sectional shape perpendicular to the axial direction) is substantially the shape of a triangle formed by recessing three portions of an annular outer circumference (shown by a long-short dashed line in FIG. 2), whose center is the central axis $P_0$ and which connects the convex curved corner portions 48, 50, and 52, radially inward.

Accordingly, the lateral cross sectional area of the rear section of the catheter member 10 is smaller than the lateral cross sectional area of conventional catheters having an annular transverse profile. The three lateral faces 54, 56, and 58 positioned corresponding to the three bases $R_1$, $R_2$, and $R_4$ of the transverse triangular provide in the rear section of the catheter member 10 are provided as recessed portions formed extending contiguously over the entire length in the axial direction in the outer circumferential surface of the rear end section of the catheter member 10.

It should be noted that in the rear section of the catheter member 10 having such an outer circumferential shape, the distance $X_1$ from the tip of the convex curved corner portion 52 positioned on the side on which the extrusion aperture 22 is formed to the lateral face 58 in opposition thereto, which is the largest width in the direction of extrusion of the needle-shaped tube member 12 (down in FIG. 2), is approximately 1.5 mm. Also, the distance $Y_1$ between the tips of the two convex curved corner portions 48 and 50 at either end of the lateral face 58, which is the largest width in the direction perpendicular to the direction of extrusion of the needle-shaped tube member 12 (the left to right direction in FIG. 2), is approximately 2.0 mm. Thus, the width of the rear end portion of the catheter member 10 is larger than the distance in the extrusion direction of the needle-shape tube member 12. This makes it possible to easily bend the catheter member 10 in the direction of extrusion of the needle-shaped tube member 12.

Moreover, in the rear section of the catheter member 10, of the three lateral faces 54, 56, and 58, the lateral face 58 positioned corresponding to the base $R_4$ that links the two apexes $Q_1$ and $Q_2$ corresponding to the central axes $P_1$ and $P_2$ of the first lumen 18a and the second lumen 18b, respectively, that is, the lateral face 58 extending perpendicular to the direction in which the needle-shaped tube member 12 is extruded from the extrusion aperture 22 and in opposition to the convex curved corner portion 52, which is positioned on the side on which the extrusion aperture 22 is formed, is a curved surface whose curvature is small. Thus, when the needle-shaped tube member 12 penetrates cardiac muscle, the reaction force causes the curved lateral face 58 of the catheter member 10 to come into contact the inner wall surface of the blood vessel over the largest area. Also, the two lateral faces 54 and 56 other than the lateral face 58, which is a curved surface, both have flat surfaces. Thus, the lateral cross sectional area of the rear section of the catheter member 10 is made as small as possible.

On the other hand, as shown in FIG. 5, the second lumen 18b is not formed in the front section of the catheter member 10, or in other words, the site more forward than the site where the lateral aperture 24 is formed in the catheter member 10. Thus, the front section of the catheter member 10, in cross section, has three convex curved corner portions 60, 62, and 64 respectively positioned corresponding to the apexes $Q_1$, $Q_3$, and $Q_4$ of a triangle B (shown by a long-short dashed line in FIG. 5) whose apexes are the central axes (center points) $P_1$, $P_3$, and $P_4$ of the first lumen 18a, the third lumen 18c, and the fourth lumen 18d, and has three lateral faces 66, 68, and 70 positioned corresponding to the three bases $R_1$, $R_3$, and $R_4$ of the triangle B. Of the three convex curved corner portions 60, 62, and 64, adjacent portions are connected by the three lateral faces 66, 68, and 70.

Thus, the outer circumferential surface shape of the front section of the catheter member 10 is substantially the shape of a triangle whose corner portions have been rounded. Further, the outer circumference shape of the front section of the catheter member 10 is smaller than that of the rear section of the catheter member 10. In other words, the transverse profile of the front section of the catheter member 10 is substantially the shape of a triangle, in which an annular outer circumference (shown by a long-short dashed line in FIG. 5) whose center is the central axis $P_0$ and which connects the two convex curved corner portions 60 and 64, is formed significantly more recessed than the rear section of the catheter member 10.

Accordingly, the lateral cross sectional area of the front section of the catheter member 10 is even smaller than the lateral sectional area of the rear section. Thus, the geometrical moment of inertia in the front section of the catheter member 10 is lowered, thereby increasing the flexibility. In the front section of the catheter member 10, the three lateral faces 66, 68, and 70 positioned corresponding to the three bases $R_1$, $R_3$, and $R_4$ of the transverse triangular shape are provided as recessed portions formed extending contiguously over the entire length in the axial direction in the outer circumferential surface of the front section of the catheter member 10. That is, the lateral face 66 is smoothly connected to the lateral face 54. Also, the lateral face 68 and the lateral face 56 in practice are the same lateral face. Moreover, the lateral face 70 is connected to the lateral face 58.

It should be noted that in the front section of the catheter member 10 having such an outer circumferential shape, the distance $X_2$ from the tip of the convex curved corner portion 64 positioned on the side on which the extrusion aperture 22 is formed to the lateral face 70 in opposition thereto, which has the largest width in the direction of extrusion of the needle-shaped tube member 12, is approximately 1.5 mm. Also, the distance $Y_2$ between the tips of the convex curved corner portions 60 and 62 at either end of the lateral face 70, which is the largest width in the direction perpendicular to the direction of extrusion of the needle-shaped tube member 12, also is approximately 1.5 mm.

Moreover, in the front section of the catheter member 10, of the three lateral faces 66, 68, and 70, the lateral face 70 positioned corresponding to the base $R_4$ that links the two apexes $Q_1$ and $Q_3$ that correspond to the central axes $P_1$ and $P_3$ of the first lumen 18a and the third lumen 18c, respectively, that is, the lateral face 70 in opposition to the convex curved corner portion 64 in which the extrusion aperture 22 is formed and extending perpendicular to the direction in which the needle-shaped tube member 12 is extruded from the extrusion aperture 22, is a curved surface whose curvature is small. Thus, when the needle-shaped tube member 12 penetrates cardiac muscle, the reaction force causes the curved lateral face 70 of the catheter member 10 to come into contact with the inner wall surface of the blood vessel over the largest area. Also, the two lateral faces 66 and 68 other than the lateral face 70, which is a curved surface, both have flat surfaces. Thus, the lateral cross sectional area of the front section of the catheter member 10 is made as small as possible.

A method for infusing a predetermined reagent into a lesion portion such as nearly or substantially necrotic cardiac muscle using the infusion catheter of the present embodiment with the above structure is described next.

Figure 6:
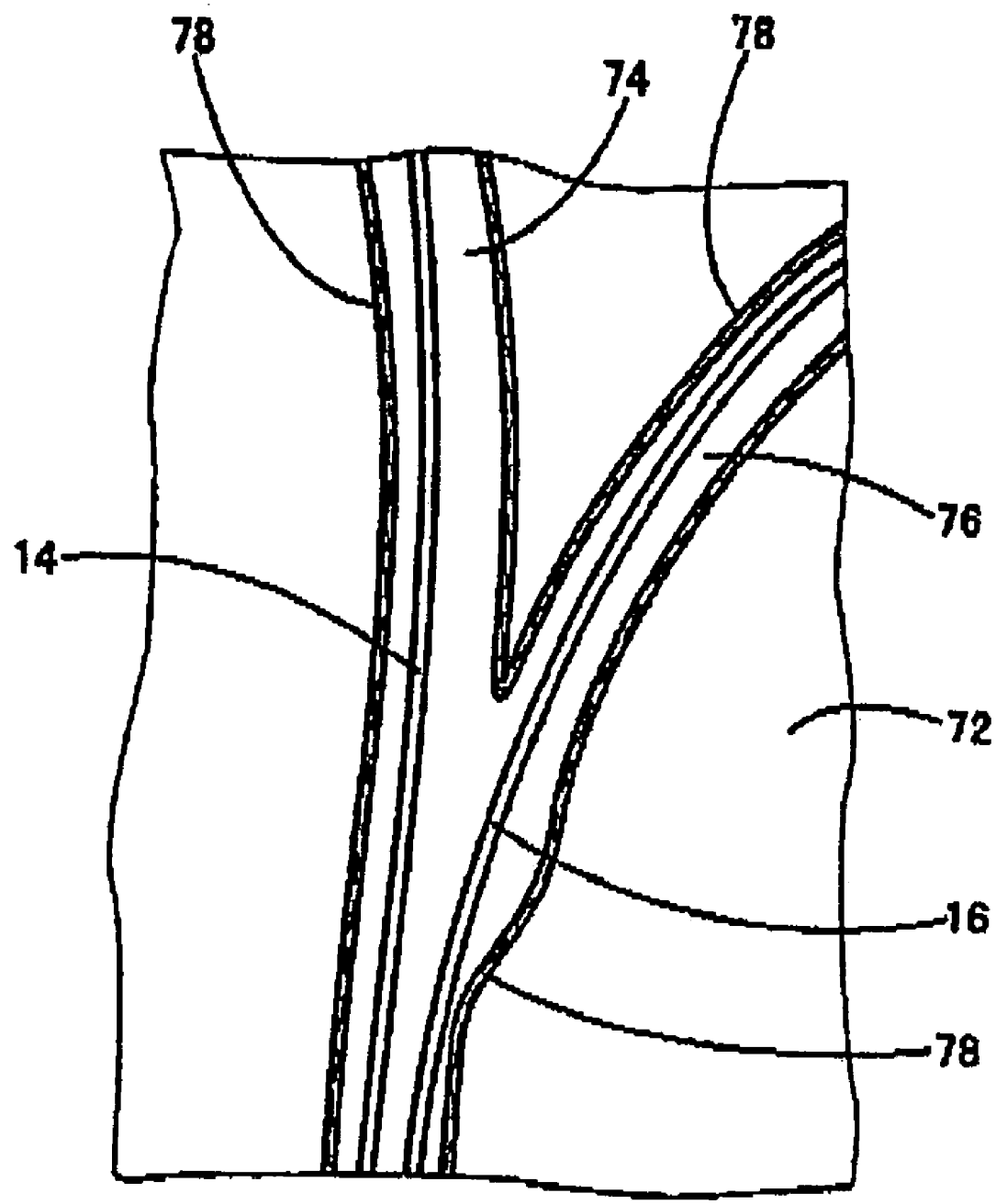
FIG. 6 is a diagram showing an example of how a predetermined reagent is infused into a lesion portion of cardiac muscle using the infusion catheter shown in FIG. 1, and shows a state where the first guide wire and the second guide wire have been inserted into a primary blood vessel and a branch blood vessel on the surface of the cardiac muscle.

When performing a reagent infusion treatment using this infusion catheter, first, as shown in FIG. 6, the first guide wire 14 is inserted into a primary blood vessel 74 on the surface of cardiac muscle 72. The second guide wire 16, in contrast, is inserted into a branch blood vessel 76 on the surface of the cardiac muscle 72 that has branched from the primary blood vessel 74. It should be noted that in general the first and the second guide wires 14 and 16 are inserted into the primary blood vessel 74 and the branch blood vessel 76 by hand.

Next, the catheter member 10 is inserted into the primary blood vessel 74 on the surface of the cardiac muscle 72 along the first guide wire 14. While the catheter member 10 is inserted into the primary blood vessel 74, the position of the marker tube 46 provided on the outside of the front end portion in the direction of insertion of the catheter member 10 on a monitor or the like is confirmed using radiation. That is, once the marker tube 46 has arrived at a predetermined area of the primary blood vessel 74 by threading the catheter member 10 through the primary blood vessel 74, threading of the catheter member 10 is temporarily halted. Then, after confirming the position of the shortest site or the longest site of the marker tube 46, the catheter member 10 is rotated about its axis while fine tuning its axial position within the primary blood vessel 74 in order to position the extrusion aperture 22 such that it opens toward the lesion portion at a predetermined position of the lesion portion of the cardiac muscle 72 to which the reagent is to be infused.

It should be noted that as discussed above, in the infusion catheter of the present embodiment the section to the rear of the spot where the lateral aperture 24 is formed and the section in front of this spot in the catheter member 10 both have a substantially triangular transverse profile, and thus the lateral cross sectional area of these sections is effectively small. It is accordingly easy to insert the catheter member 10 into the primary blood vessel 74.

Moreover, the lateral cross sectional area of the front section is smaller than the lateral cross sectional area of the rear section of the catheter member 10, and this increases the flexibility of the front section. Thus, damage to the inner wall surface of the primary blood vessel 74 when inserting the catheter member 10 into the primary blood vessel 74 can be effectively prevented.

Furthermore, the rear section of the catheter member 10 has the lateral face 58, which is a curved surface whose curvature is small, and the two flat lateral faces 54 and 56. On the other hand, the front section of the catheter member 10 also has the lateral face 70, which is a curved surface whose curvature is small, and the two flat lateral faces 66 and 68. For that reason, when the catheter member 10 is inserted into the primary blood vessel 74, a gap is formed between the lateral faces 54, 56, 58, 66, 68, and 70 and the inner wall surface of the primary blood vessel 74. Thus, blood can reliably flow through the gap formed between the lateral faces 54, 56, 58, 66, 68, and 70 and the inner wall surface of the primary blood vessel 74 when the catheter member 10 has been inserted into the primary blood vessel 74.

Figure 7:
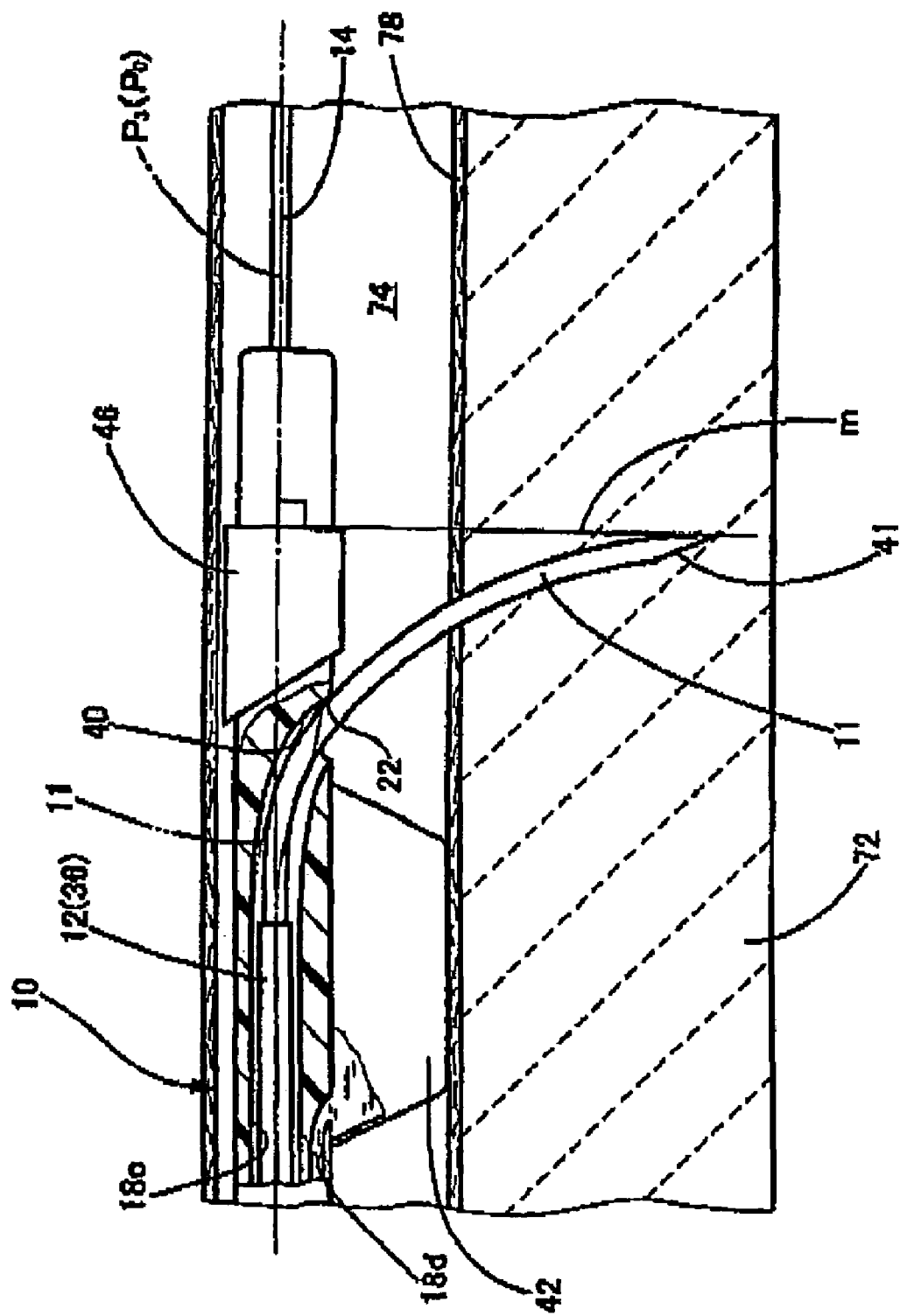
FIG. 7 is a diagram showing another example of how a predetermined reagent is infused into a lesion portion of cardiac muscle using the infusion catheter shown in FIG. 1, and shows a state where the needle portion has penetrated the cardiac muscle.

Next, as shown in FIG. 7, once the catheter member 10 has been positioned at the foregoing predetermined position within the primary blood vessel 74, physiological saline solution or the like is introduced into the fourth lumen 18d within the catheter member 10 from the syringe 44, expanding the balloon 42 toward the direction in which the extrusion aperture 22 opens. By doing this the catheter member 10 is fixedly retained within the primary blood vessel 74 at the lesion portion of the cardiac muscle 72 to which the reagent is to be infused. It should be noted that at this time the gap between the lateral faces 54, 56, 58, 66, 68, and 70 and the inner wall surface of the primary blood vessel 74 is secured. Thus, even when the balloon 42 has expanded it is possible to favorably ensure the flow of blood within the primary blood vessel 74.

Next, the needle-shaped tube member 12 is moved within the third lumen 18c forward in the direction in which the catheter member 10 is inserted into the primary blood vessel 74. When the needle portion 11 of the tip of the needle-shaped tube member 12 has arrived at the front end portion within the third lumen 18c, the needle portion 11 is slid along the guide surface 40 provided in the inner circumference portion of the front end portion of the third lumen 18c while it is smoothly advanced toward the extrusion aperture 22, as shown by the long-short dashed line in FIG. 7. Then, by further moving the needle-shaped tube member 12 forward, the needle portion 11 is extruded through the extrusion aperture 22 as shown by the solid line in FIG. 7. The operation of extruding the needle portion 11 by moving the needle-shaped tube member 12 is carried out manually or using a screw mechanism, for example, that is known to the public.

It should be noted that as mentioned above, in the infusion catheter of the present embodiment, the needle portion 11 of the needle-shaped tube member 12 is extruded from the extrusion aperture 22 in a direction that is substantially perpendicular to the direction in which the first guide wire 14 and the second guide wire 16 are extended from the tip opening 20 and the lateral aperture 24, respectively, of the catheter member 10. Also, here the first guide wire 14 and the second guide wire 16 that have been extended through the tip opening 20 and the lateral aperture 24, respectively, of the catheter member 10 are inserted into the primary blood vessel 74 and the branch blood vessel 76, respectively, running over the surface of the cardiac muscle 72. Thus, the plane formed by the first and second guide wires 14 and 16 is substantially approximate to the surface of the cardiac muscle 72.

Consequently, through the operation discussed above, the needle portion 11 of the needle-shaped tube member 12 that has been extruded from the extrusion aperture 22 of the catheter member 10 is extruded substantially perpendicularly to the surface of the cardiac muscle 72. Moreover, the needle portion 11, as discussed above, has a curved shape that curves in the direction of extrusion from the extrusion aperture 22 in the movement direction of the needle-shaped tube member 12, and thus when it has been extruded from the extrusion aperture 22, it is disposed such that the tangent m of its tip region is perpendicular to the central axis $P_0$ of the catheter member 10. It should be noted that strictly speaking, "substantially perpendicular" here is used taking into account that there may be cases in which the needle portion 11 is not extruded perpendicular to the surface of the cardiac muscle 72 because, in practice, the cardiac muscle 72 has a complex shape.

Consequently, due to this operation, the needle portion 11 of the needle-shaped tube member 12 that has been extruded from the extrusion aperture 22 of the catheter member 10 is passed through a blood vessel wall 78 of the primary blood vessel 72 and penetrates a predetermined spot of a lesion portion of the cardiac muscle 72. Then, as the needle-shaped tube member 12 is moved forward within the catheter member 10, the needle portion 11 is advanced substantially perpendicular with respect to the surface of the cardiac muscle 72 until reaching a predetermined depth of the lesion portion.

When advancing the needle portion 11 into the lesion portion, most of the reaction force with respect to advancing the needle portion 11 into the cardiac muscle 72 in the direction opposite the direction in which the needle portion 11 is advancing, that is, in the direction perpendicular to the surface of the cardiac muscle 72, is applied to the catheter member 10 via the needle portion 11. However, here the first guide wire 14 and the second guide wire 16 are inserted into and positioned in the primary blood vessel 74 and the branch blood vessel 76 on the surface of the cardiac muscle 72, and thus this reaction force is divided between the first guide wire 14 and the second guide wire 16 and can be adequately and reliably received. Consequently, due to the present operation, the needle portion 11 can be very smoothly and reliably advanced to a predetermined depth of the lesion portion of the cardiac muscle 72.

It should be noted that, as discussed above, the rear section of the catheter member 10 is more easily bent in the direction of extrusion of the needle-shaped tube member 12 than in the direction perpendicular to this direction. For that reason, when inserting the catheter member 10 into the primary blood vessel 74, the catheter member 10 is easily bent following the surface of the cardiac muscle 72, making insertion of the catheter member 10 into the primary blood vessel 74 easy. Also, when the needle portion 11 has penetrated the lesion portion of the cardiac muscle 72, the rear section of the catheter member 10 is easily bent in the extrusion direction of the needle-shaped tube member 12, allowing some of the rear section and the area in front of that portion of the catheter member 10 to be brought into contact with the inner wall surface of the primary blood vessel 74 at the lateral faces 58 and 70, which are curved large-area portions, on the side opposite the extrusion direction of the needle-shaped tube member 12.

Consequently, when the needle portion 11 of the needle-shaped tube member 12 penetrates the lesion portion of the cardiac muscle 72 and is advanced through this operation, that reaction force is favorably and efficiently received by the two lateral faces 58 and 70, which are curved surfaces, of the catheter member 10 without damaging the inner wall surface of the primary blood vessel 74.

Next, movement of needle-shaped tube member 12 is ended once the needle portion 11 has been advanced up to a predetermined depth position of the lesion portion of the cardiac muscle 72. A reagent including cells or growth factor, for example, aimed at regenerating the cardiac muscle 72 is then introduced into the inner lumen of the needle-shaped tube member 12 from the syringe 44 that is connected to the connector 32 at the proximal side of the needle-shaped tube member 12. This reagent is then infused into the lesion portion of the cardiac muscle 72 by ejecting it from the tip opening of the needle portion 11.

Once the reagent has been infused to an area of the lesion portion of the cardiac muscle 72, the needle-shaped tube member 12 is retreated within the catheter member 10, drawing the needle portion 11 into the catheter member 10. This operation of infusing a reagent to a lesion portion of the cardiac muscle 72 is repeated a plurality of times at other locations, and by doing so the reagent is infused to a plurality of areas of the lesion portion of the cardiac muscle 72.

In this way, the infusion catheter of the present embodiment has a catheter member 10 whose outer circumferential shape is substantially triangular with rounded corner portions, and as such the lateral cross sectional area of the catheter member 10 is suitably small. Thus, the catheter member 10 can be more smoothly and easily inserted into the primary blood vessel 74 than if a conventional infusion catheter, for example, whose a catheter member 10 has an annular transverse profile, is inserted into the primary blood vessel 74.

Moreover, with this infusion catheter, when the catheter member 10 has been inserted into the primary blood vessel 74, a gap is formed between the three lateral faces 54, 56, and 58 of the rear section thereof and the inner wall surface of the primary blood vessel 74 and between the three lateral faces 66, 68, and 70 of the front section thereof and the lateral wall surface of the primary blood vessel 74, allowing the flow of blood to be favorably secured. Further, the front section of the catheter member 10 has a smaller lateral cross sectional area than its rear section. This allows the flow of blood within the primary blood vessel 74 to be more effectively secured when the catheter member 10 has been inserted. Consequently, the task of infusing a predetermined reagent into a lesion portion of the cardiac muscle 72 can be carried out more safely.

With the infusion catheter of the present embodiment, the needle portion 11 extruded from the extrusion aperture 22 of the catheter member 10 can be reliably penetrated into a predetermined location of the lesion portion of the cardiac muscle 72. Moreover, most of the reaction force that is generated by the needle portion 11 penetrating the cardiac muscle 72 is adequately and reliably received by the first guide wire 14 and the second guide wire 16, which are inserted into the primary blood vessel 74 and the branch blood vessel 76 on the surface of the cardiac muscle 72, and thus the needle portion 11 can be very smoothly and reliably advanced up to a predetermined depth position of the lesion portion of the cardiac muscle 72.

Thus, if the infusion catheter of the present embodiment described above is used, then the needle portion 11 can reliably penetrate the lesion portion at a predetermined position up to a desired depth, even if the lesion portion of the cardiac muscle 72 is hard. As a result, the effect of treatment or a procedure in which a predetermined reagent for regenerating the cardiac muscle 72 is infused into a lesion portion of the cardiac muscle 72 can be more adequately increased.

Further, with the infusion catheter of the present embodiment, the first guide wire 14 is inserted into the first lumen 18a from the insertion aperture 34 provided opening laterally in the rear end portion of the catheter member 10 and extended directly forward axially through the tip opening 20 of the catheter member 10. Also, the second guide wire 16 is inserted directly into the second lumen 18b from the opening of the connector 26 attached to the rear end portion of the catheter member 10, and is extended laterally through the lateral aperture 24, which is provided opening laterally, in the front end portion of the catheter member 10.

Thus, with this infusion catheter, the first guide wire 14 and the second guide wire 16 both are threaded through the catheter member 10 bent or curved at only one position. Consequently, there is relatively little resistance to sliding the guide wires 14 and 16 through the catheter member 10, and this allows the guide wires 14 and 16 to be threaded through the catheter member 10 more smoothly.

Furthermore, with the infusion catheter according to the present embodiment, the third lumen 18c into which the needle-shaped tube member 12 is inserted and arranged is disposed such that its central axis $P_3$ matches the central axis $P_0$ of the catheter member 10. Thus, the infusion catheter has good overall balance, and accordingly the task of infusing a reagent to a lesion portion of the cardiac muscle 72 can be performed more stably.

Further, with this infusion catheter, the extrusion aperture 22 is arranged in such a manner that the center point $O_3$ of the extrusion aperture 22 through which needle portion 11 of the needle-shaped tube member 12 is extruded is positioned on the plane β, which is perpendicular to the plane α including the central axis $P_3$ of the third lumen 18c into which the needle-shaped tube member 12 is inserted and arranged and the central axis $P_0$ of the catheter member 10 matching the central axis $P_3$, and also including the central axes $P_1$ and $P_2$ of the first and second lumens 18a and 18b into which the first and second guide wires 14 and 16 are respectively inserted and arranged. Thus, it provides a favorable balance in the arrangement of the needle-shape tube member 12 in the catheter member 10 and stability during the operation when extruding the needle portion 11 from the extrusion aperture 22. As a result, the task of infusing a reagent to a lesion portion of the cardiac muscle 72 can be performed even more stably and smoothly.

Further, with the infusion catheter according to the present embodiment, the central axes $P_1$ and $P_2$ of the first and second lumens 18a and 18b into which the first and second guide wires 14 and 16 are respectively inserted and arranged, the central axis $P_3$ of the third lumen 18c into which the needle-shaped tube member 12 is inserted and arranged, and the central axis $P_0$ of the catheter member 10 are positioned on a single plane α, and the first and second lumens 18a and 18b are disposed on either side of the third lumen 18c and sandwich it between them. Thus, the distance between the first lumen 18a and the second lumen 18b is made as large as possible, and this allows the distance between the first guide wire 14 and the second guide wire 16, which are extended to the outside through the tip opening 20 and the lateral aperture 24 of the catheter member 10 from the two lumens 18a and 18b, to be made large also. As a result, most of the reaction force that is generated when the needle portion 11 is inserted into a lesion portion of the cardiac muscle 72 can be more adequately and reliably received and stopped by the first guide wire 14 and the second guide wire 16.

With this infusion catheter, the fourth lumen 18d for conducting fluid for expanding the balloon 42 that is provided outside the catheter member 10 is disposed in such a manner that its central axis $P_4$ is positioned on the plane β, which includes the central axis $P_3$ of the third lumen 18c into which the needle-shaped tube member 12 is inserted and arranged, the central axis $P_0$ of the catheter member 10, and the center point $O_3$ of the extrusion aperture 22. This also results in a good overall balance of the infusion catheter, and thus the task of infusing a reagent to a lesion portion of the cardiac muscle 72 can be performed more stably.

Furthermore, in the infusion catheter of the present embodiment, the inner circumferential surface of the front end portion of the third lumen 18c, into which the needle-shaped tube member 12 is inserted and arranged, serves as the guide surface 40, which is a convex curved surface that is curved axially forward in the direction in which the extrusion aperture 22 is provided, and the needle portion 11 of the needle-shaped tube member 12 also has a curved shaped that corresponds to the guide surface 40. For that reason, the needle portion 11 can be smoothly and reliably extruded from the extrusion aperture 22 in the direction perpendicular to the surface of the cardiac muscle 72 in conjunction with forward movement of the needle-shaped tube member 12 within the catheter member 10. Due to this structure as well, the task of infusing a reagent to a lesion portion of the cardiac muscle 72 can be performed even more stably and smoothly.

The positions where the first through fourth lumens 18a to 18d provided within the catheter member 10 are arranged and the outer circumferential shape of the catheter member 10 are not limited to the example discussed above, however.

Figure 8:
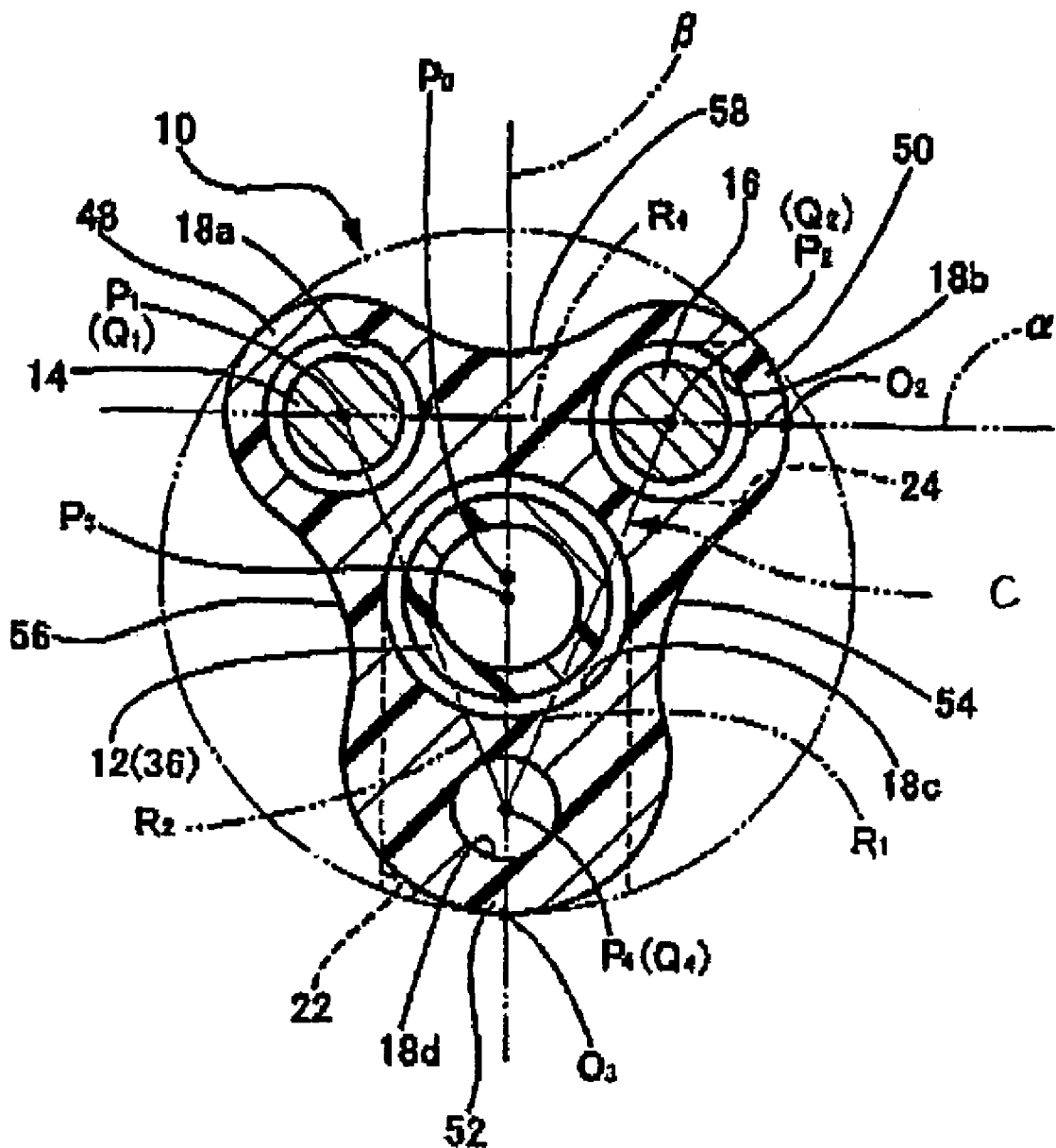
FIG. 8 is a diagram that corresponds to FIG. 2 and shows another example of an infusion catheter having a structure according to the present invention.

For example, as shown in FIG. 8, it is also possible to dispose the third lumen 18c such that its central axis $P_3$ is positioned shifted in the radial direction of the catheter member 10 from the central axis $P_0$ of the catheter member 10 toward the side where the extrusion aperture 22 is formed, and the first and second lumens 18a and 18b are disposed such that the plane α including their central axes $P_1$ and $P_2$ is shifted in the radial direction of the catheter member 10 from the central axis $P_0$ of the catheter member 10 toward the side opposite the side where the extrusion aperture 22 is formed.

In this manner it is possible to adopt a configuration having an outer circumferential surface shape in which the three lateral faces 54, 56, and 58, which are positioned corresponding to the bases $R_1$, $R_2$, and $R_4$ of a triangle C (shown by a long-short dashed line in FIG. 8) whose apexes are the central axes (center points) $P_1$, $P_2$, and $P_4$ of the first and second lumens 18a and 18b thus disposed and the fourth lumen 18d.

Figure 9:
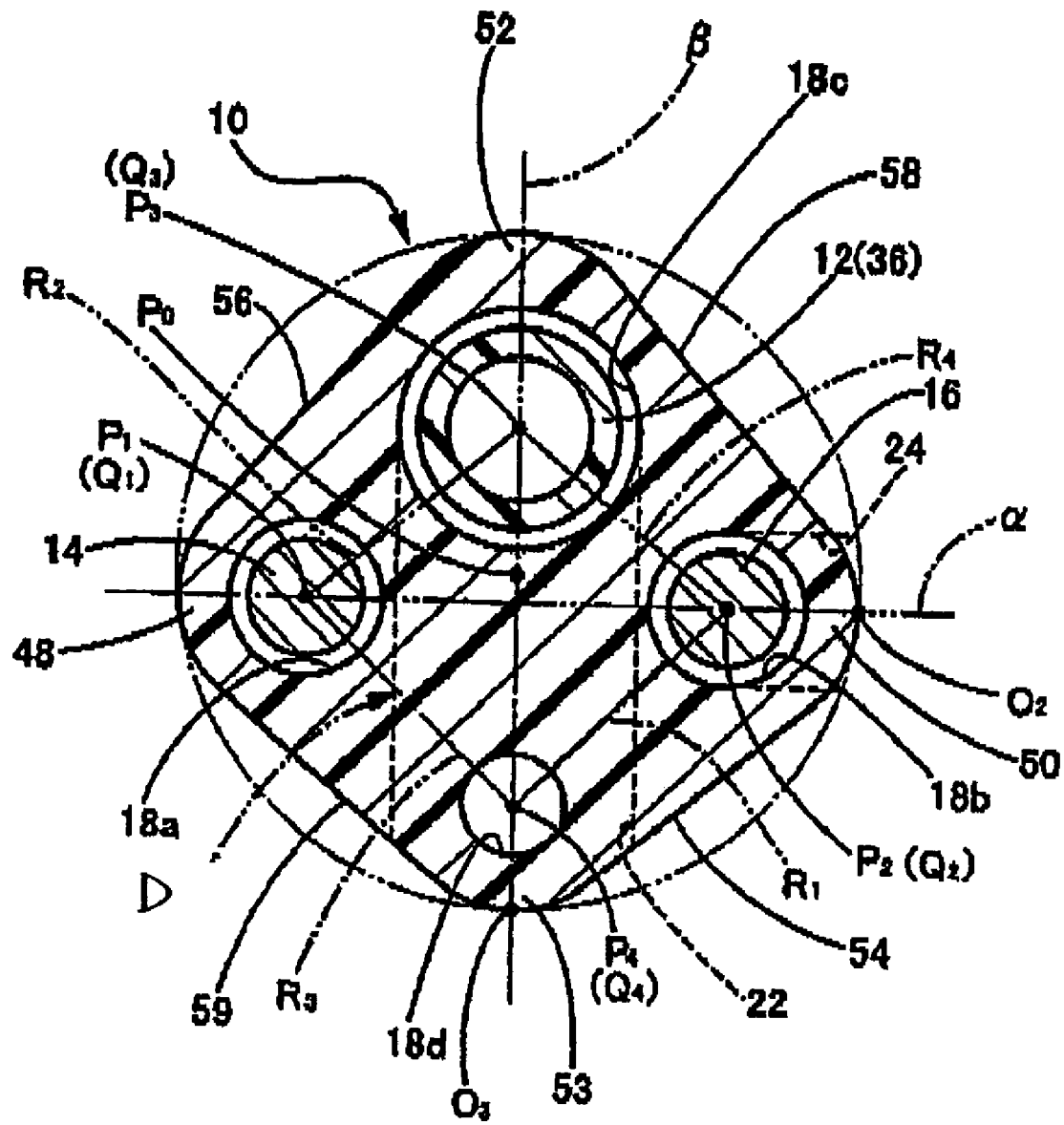
FIG. 9 is a diagram that corresponds to FIG. 2 and shows yet another example of an infusion catheter having a structure according to the present invention.

Further, as shown in FIG. 9, it is also possible to dispose the third lumen 18c such that its central axis $P_3$ is positioned shifted in the radial direction of the catheter member 10 from the central axis $P_0$ of the catheter member 10 toward the side opposite the side where the extrusion aperture 22 is formed, and the first and second lumens 18a and 18b are disposed such that the plane α including their central axes $P_1$ and $P_2$ is shifted in the radial direction of the catheter member 10 from the central axis $P_0$ of the catheter member 10 toward the side where the extrusion aperture 22 is formed.

In this manner it is possible to adopt a configuration having a substantially rectangular outer circumferential shape provided with four convex curved corner portions 48, 50, 52, and 53 positioned corresponding to the apexes $Q_1$ to $Q_4$ of a rectangle D (shown by a long-short dashed line in FIG. 9) whose apexes are the central axes (center points) $P_1$ to $P_4$ of the first through fourth lumens 18a and 18d disposed in this manner, and four flat lateral faces 54, 56, 58, and 59 that are positioned corresponding to the bases $R_1$ to $R_4$ of the rectangle D and connect the four convex curved corner portions 48, 50, 52, and 53.

In the two embodiments having the structures shown in FIG. 8 and FIG. 9, the transverse profile of the catheter member 10 is smaller than an annular shape (shown by a long-short dashed line in FIG. 8 and FIG. 9) whose center is the central axis $P_0$ and whose radius is the apex of the convex curved corner portion farthest from the central axis $P_0$. Also, the lateral faces 54, 56, 58, and 59 of the catheter member 10 are provided as recessed portions extending contiguously over the entire length in the axial direction in the outer circumferential surface of the catheter member 10. Furthermore, the needle portion 11 of the needle-shaped tube member 12 can be extruded in the direction perpendicular to the direction of extrusion of the first guide wire 14 and the second guide wire 16. Consequently, the same operations and effects as in the first embodiment can be obtained effectively with the second and third embodiments as well.

Figure 10:
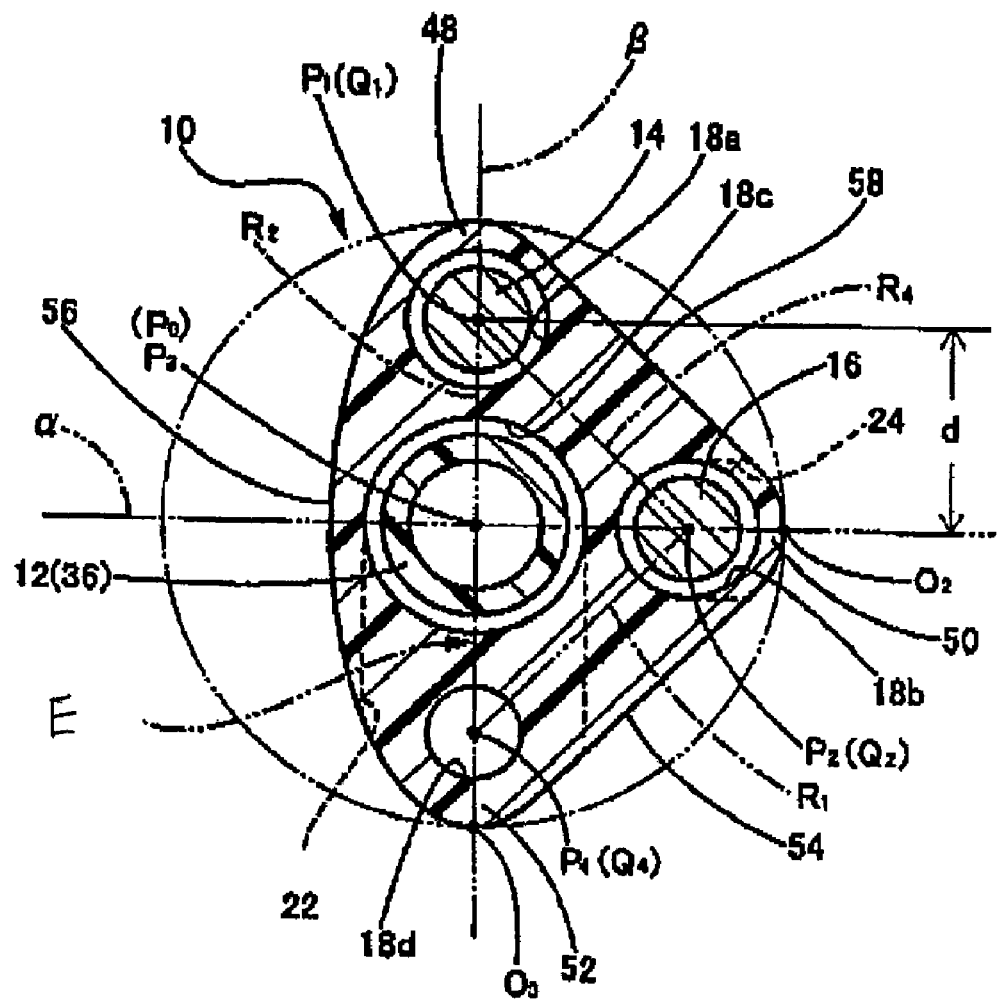
FIG. 10 is a diagram that corresponds to FIG. 2 and shows a further example of an infusion catheter having a structure according to the present invention.

Further, as shown in FIG. 10, the third lumen 18c is disposed coaxially with the catheter member 10, whereas the first lumen 18a is disposed such that its central axis $P_1$ is positioned on the side opposite the side on which the center point $O_3$ of the extrusion aperture 22 is provided, sandwiching the central axis $P_3$ of the third lumen 18c between them, on a plane β including the central axis $P_3$ of the third lumen 18c, the central axis $P_0$ of the catheter member 10, and the center point $O_3$ of the extrusion aperture 22. Moreover, the second lumen 18b is disposed such that its central axis $P_2$ is positioned on a plane α, which includes the central axis $P_3$ of the third lumen 18c and the central axis $P_0$ of the catheter member 10 and which is perpendicular to the plane β.

In this manner it is possible to achieve a configuration having an outer circumferential shape provided with the three lateral faces 54, 56, and 58, which are positioned corresponding to the bases $R_1$, $R_2$, and $R_4$ of a triangle E (shown by a long-short dashed line in FIG. 10) whose apexes are the central axes (center points) $P_1$, $P_2$, and $P_4$ of the first and second lumens 18a and 18b thus disposed and the fourth lumen 18d.

Figure 11:
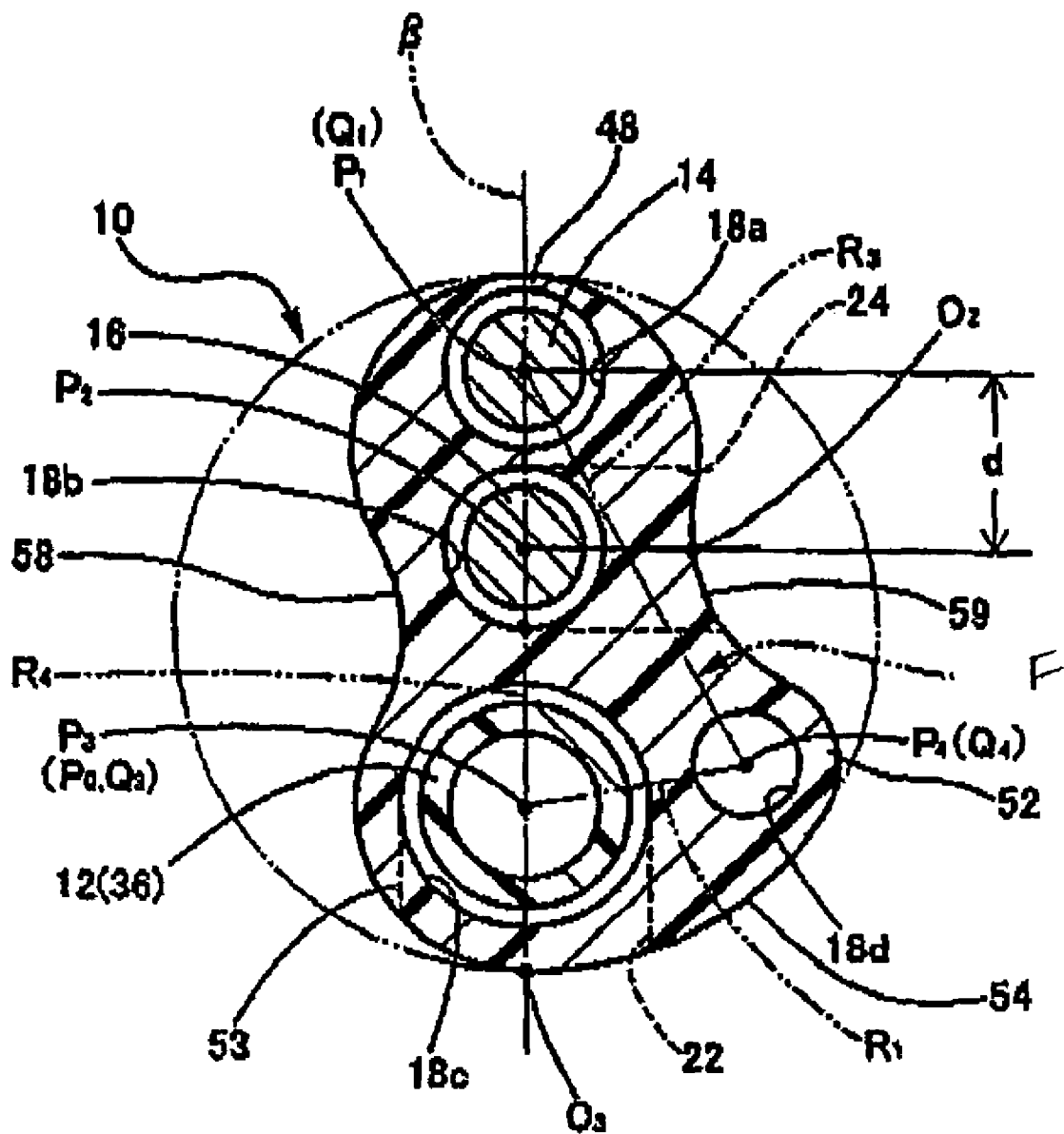
FIG. 11 is a diagram that corresponds to FIG. 2 and shows a yet further example of an infusion catheter having a structure according to the present invention.

Further, as shown in FIG. 11, it is also possible to arrange the first, second, and third lumens 18a to 18c such that their respective central axes (center points) $P_1$ to $P_3$ are positioned on a plane β, which includes the central axis $P_0$ of the catheter member 10 and the center point $O_3$ of the extrusion aperture 22. Also, the fourth lumen 18d can be disposed at a position that is different from the positions where it is disposed in the first through third embodiments.

In this manner, it is possible to adopt a configuration having an outer circumferential shape provided with three lateral faces 54, 58, and 59, which are positioned corresponding to the bases $R_1$, $R_3$, and $R_4$ of a triangle F (shown by a long-short dashed line in FIG. 11) whose apexes are the central axes (center points) $P_1$, $P_3$, and $P_4$ of the first lumen 18a, the third lumen 18c, and the fourth lumen 18d disposed in this manner, and in which of these lateral faces, the two lateral faces 58 and 59 are concave curved surfaces.

In the two embodiments having the structures shown in FIG. 10 and FIG. 11, the transverse profile of the catheter member 10 is smaller than an annular shape (shown by a long-short dashed line in FIG. 10 and FIG. 11) whose center is the central axis $P_0$ and whose radius is the apex of the convex curved corner portion farthest from the central axis $P_0$. Also, the lateral faces 54, 56, 58, and 59 of the catheter member 10 are provided as recessed portions extending contiguously over the entire length in the axial direction in the outer circumferential surface of the catheter member 10. Thus, the catheter member 10 can be easily inserted into the primary blood vessel 74, and while inserted therein, the flow of blood through the primary blood vessel 74 can be favorably secured.

In these two embodiments the first lumen 18a and the second lumen 18b are displaced and parallel to one another, and have a deviation d in the radial direction of the catheter member 10 between the positions where their respective central axes $P_1$ and $P_2$ are disposed. This deviation d, however, it is a very short length, and is smaller than the radius of the catheter member 10. For that reason, there is substantially no difference in the points of intersection between the extension direction vectors of the first and second guide wires 14 and 16 inserted and arranged in the first and second lumens 18a and 18b, respectively, and thus the needle-shaped tube member 12 is substantially extruded in the plane including these direction vectors. Consequently, this tiny deviation d has hardly any effect.

Thus, in the fourth and fifth embodiments described above, the needle portion 11 of the needle-shaped tube member 12 can be extruded in a direction that is substantially perpendicular to the direction in which the first and the second guide wires 14 and 16 are extruded. The same operations and effects as in the first embodiment can therefore be obtained effectively with the fourth and fifth embodiments as well.

Specific configurations of the present invention have been described in detail above, but these are only illustrative examples, and the present invention is in no way restricted by the foregoing description.

Figure 12:
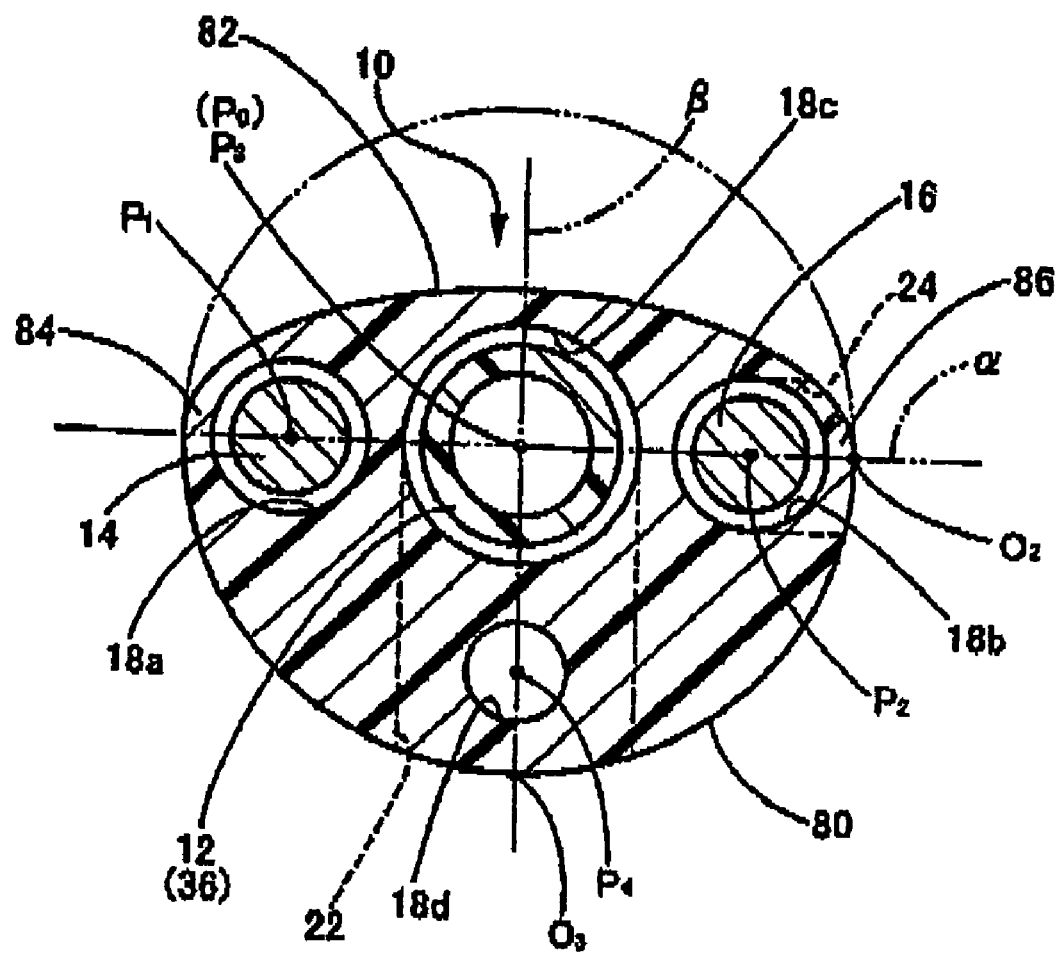
FIG. 12 is a diagram that corresponds to FIG. 2 and shows another example of an infusion catheter having a structure according to the present invention.

For example, there is no limitation to the number indicated in the foregoing embodiments regarding the convex curved corner portions or the lateral faces providing the outer circumferential surface of the catheter member 10. That is, as shown in FIG. 12, it is also possible to adopt a configuration in which the outer circumferential surface is constituted by the two lateral faces of a substantially semi-annular lateral face 80 and a lateral face 82 made of a convex curved surface with small curvature, and two convex curved corner portions 84 and 86. It is of course also possible to achieve the catheter member 10 using an outer circumferential shape having five or more lateral faces or convex curved corner portions.

As long as concave portions extending axially are formed in the outer circumferential surface of the catheter member 10 such that the sectional shape of the catheter member 10 perpendicular to its axial direction is a shape in which at least a portion of the outer circumference of an annular shape has been recessed radially, then the outer circumferential shape of the catheter member 10 is not absolutely limited to the configurations that have been provided for illustration.

Also, it is not absolutely necessary that the recessed portions formed in the outer circumferential surface of the catheter member 10 are formed extending contiguously over the entire length of the catheter member 10. Thus, for example, it is of course also possible to adopt a configuration in which recessed portions are formed intermittently over the entire length of the outer circumferential surface of the catheter member 10, or a configuration in which, in the catheter member 10, recessed portions are not provided in the outer circumferential surface of portions that are not inserted into the body.

Moreover, it is only necessary that any three of the first through fourth lumens 18a to 18d are formed within the catheter member 10.

Furthermore, there is nothing preventing the adoption of a shape in which the guide surface 40 made of a convex curved surface is formed in the inner circumferential surface of the front end portion of the third lumen 18 but the needle portion 11 is provided with a straight shape.

Also, in the above embodiments, the open end surface 41 of the needle portion 11 is a slanted surface that is slanted in the extrusion direction of the needle portion 11 toward the direction in which the needle-shaped tube member 12 moves when the needle portion 11 is extruded from the extrusion aperture 22 (in FIG. 1, the lower side of the needle portion 11 is the slanted surface). However, alternatively it is also possible to provide the open end surface 41 as a slanted surface that is slanted in the extrusion direction of the needle portion 11 toward the direction that is opposite the direction in which the needle-shaped tube member 12 is moved when the needle portion 11 is extruded from the extrusion aperture 22 (in FIG. 1, the upper side of the needle portion 11 is the slanted surface). It should be noted that with the configuration of the present embodiment (in which the open end surface 41 is a slanted surface on the lower side of the needle portion 11 in FIG. 1), damage to or destruction of the inner circumferential surface of the third lumen 18c due to contact with the needle portion 11 when the needle portion 11 is moved within the third lumen 18c in conjunction with movement of the needle-shaped tube member 12 can be effectively prevented.

Furthermore, the balloon 42 that is provided outside the catheter member 10 is not essential to an embodiment of the present invention, and thus it is possible to omit the balloon 42. Even if the balloon 42 is provided outside the catheter member 10, the position where it is arranged is not limited to the foregoing embodiments.

In the foregoing embodiments, the needle portion 11 of the needle-shaped tube member 12 has a curved shape and the inner circumferential surface of the front end portion of the third lumen 18c is the guide surface 40, which is a convex curved surface, but the same effects can be achieved even if the needle portion 11 of the needle-shaped tube member 12 has a shape where it is extended straight.

Furthermore, the foregoing embodiments show specific examples in which the present invention is adopted for an infusion catheter for infusing a reagent to a lesion portion of cardiac muscle. The present invention, however, can of course also be favorably adopted in an embodiment for infusion catheters for infusing a reagent into body tissue other than cardiac muscle and infusion devices that are for infusing a reagent to lesion portions of cardiac muscle or body tissues other than cardiac muscle but that do fit within the scope of catheters.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

As can be understood from the above description, the infusion device according to an embodiment of the present invention can be easily inserted into the body even though at least three lumens are provided within it. Also, even if the device is inserted into a blood vessel, the flow of blood within that blood vessel can be reliably ensured.

The present application claims priority under 35 U.S.C. § 119 to Japanese Patent Application No. 2003-128125, filed May 6, 2003, the disclosure of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An infusion device comprising:
    a tubular member, made of a tube member that can be inserted into a body, in which at least three lumens are provided;
    a needle-shaped tube member, made of a thin tube, which is inserted into one of the three lumens inside the tubular member such that the needle-shaped tube member can be moved axially, and its tip is extruded outside through an extrusion aperture provided in the tubular member so as to infuse a reagent; and
    a recessed portion formed in an outer circumferential surface of the tubular member and extending in an axial direction thereof, such that a cross sectional shape of the tubular member perpendicular to the axial direction is a shape in which at least a portion of the outer circumference of an annular cross section has been recessed radially inward,
    wherein the three lumens include:
    a needle-shaped tube member lumen into which the needle-shaped tube member is inserted;
    a first guide wire lumen into which a first guide wire, that is extended from a tip of the tubular member, is inserted in such a manner that the first guide wire can be moved in the axial direction of the tubular member; and a second guide wire lumen into which a second guide wire is inserted, wherein the second guide wire is extended from the tubular member in a direction away from the first guide wire, wherein a plane that includes a central axis of the first guide wire lumen and a central axis of the second guide wire lumen is disposed such that it is perpendicular to the direction in which the extrusion aperture is formed.

2. The infusion device according to claim 1, wherein the needle-shaped tube member can be connected to a reagent supply device that supplies a reagent into the needle-shaped tube member.

3. The infusion device according to claim 1, wherein a maximum width of the tubular member in a direction of extrusion of the needle-shaped tube member from the extrusion aperture in a cross section of the tubular member taken perpendicular to its axis is smaller than a maximum width of the tubular member in a direction perpendicular to the direction of extrusion of the needle-shaped tube member in that cross section.

4. The infusion device according to claim 1, wherein a front end portion of the tubular member, in a direction of insertion into the body, is smaller in a cross section when taken perpendicular to the axial direction than in an area other than the front end portion of the tubular member.

5. The infusion device according to claim 1, wherein the tubular member further comprises in addition to the three lumens a balloon lumen for supplying fluid into a balloon that can expand and contract and that is attached to an outside portion of the tubular member.

6. An infusion device comprising:

a tubular member, made of a tube member that can be inserted into a body, in which at least three lumens are provided;

a needle-shaped tube member, made of a thin tube, which is inserted into one of the three lumens inside the tubular member such that the needle-shaped tube member can be moved axially, and its tip is extruded outside through an extrusion aperture provided in the tubular member so as to infuse a reagent; and a recessed portion formed in an outer circumferential surface of the tubular member and extending in an axial direction thereof, such that a cross sectional shape of the tubular member perpendicular to the axial direction is a shape in which at least a portion of the outer circumference of an annular cross section has been recessed radially inward, wherein the three lumens include:

a needle-shaped tube member lumen into which the needle-shaped tube member is inserted;

a first guide wire lumen into which a first guide wire, that is extended from a tip of the tubular member, is inserted in such a manner that the first guide wire can be moved in the axial direction of the tubular member; and a second guide wire lumen into which a second guide wire is inserted, wherein the second guide wire is extended from the tubular member in a direction away from the first guide wire, wherein the first guide wire lumen and the second guide wire lumen are disposed on respective sides of the needle-shaped tube member lumen and sandwich the needle-shaped tube member lumen therebetween, and central axes of the three lumens are disposed on a same plane.

7. The infusion device according to claim 6, wherein the needle-shaped tube member can be connected to a reagent supply device that supplies a reagent into the needle-shaped tube member.

8. The infusion device according to claim 6, wherein a maximum width of the tubular member in a direction of extrusion of the needle-shaped tube member from the extrusion aperture in a cross section of the tubular member taken perpendicular to its axis is smaller than a maximum width of the tubular member in a direction perpendicular to the direction of extrusion of the needle-shaped tube member in that cross section.

9. The infusion device according to claim 6, wherein a front end portion of the tubular member, in a direction of insertion into the body, is smaller in a cross section when taken perpendicular to the axial direction than in an area other than the front end portion of the tubular member.

10. The infusion device according to claim 6, wherein the tubular member further comprises in addition to the three lumens a balloon lumen for supplying fluid into a balloon that can expand and contract and that is attached to an outside portion of the tubular member.

11. An infusion device comprising:

a tubular member, made of a lube member that can be inserted into a body, in which at least three lumens are provided;

a needle-shaped tube member, made of a thin tube, which is inserted into one of the three lumens inside the tubular member such that the needle-shaped tube member can be moved axially, and its tip is extruded outside through an extrusion aperture provided in the tubular member so as to infuse a reagent; and a recessed portion formed in an outer circumferential surface of the tubular member and extending in an axial direction thereto such that a cross sectional shape of the tubular member perpendicular to the axial direction is a shape in which at least a portion of the outer circumference of an annular cross section has been recessed radially inward, wherein the three lumens include:

a needle-shaped tube member lumen into which the needle-shaped tube member is inserted;

a first guide wire lumen into which a first guide wire, that is extended from a tip of the tubular member, is inserted in such a maimer that the first guide wire can be moved in the axial direction of the tubular member; and a second guide wire lumen into which a second guide wire is inserted, wherein the second guide wire is extended from the tubular member in a direction away from the first guide wire, wherein a balloon that can expand and contract is attached to an outside portion of the tubular member; and wherein a balloon lumen for conducting fluid for expanding the balloon is provided within the tubular member, wherein a plane that includes central axes of the first guide wire lumen and the second guide wire lumen, and a plane that includes central axes of the needle-shaped tube member lumen and the balloon lumen, are disposed perpendicular to one another.

12. The infusion device according to claim 11, wherein the needle-shaped tube member can be connected to a reagent supply device that supplies a reagent into the needle-shaped tube member.

13. The infusion device according to claim 11, wherein a maximum width of the tubular member in a direction of extrusion of the needle-shaped tube member from the extrusion aperture in a cross section of the tubular member taken perpendicular to its axis is smaller than a maximum width of the tubular member in a direction perpendicular to the direction of extrusion of the needle-shaped tube member in that cross section.

14. The infusion device according to claim 11, wherein a front end portion of the tubular member, in a direction of insertion into the body, is smaller in a cross section when taken perpendicular to the axial direction than in an area other than the front end portion of the tubular member.

15. An infusion device comprising:
a tubular member, made of a tube member that can be inserted into a body, in which at least three lumens are provided;
a needle-shaped tube member, made of a thin tube, which is inserted into one of the three lumens inside the tubular member such that the needle-shaped tube member can be moved axially, and its tip is extruded outside through an extrusion aperture provided in the tubular member so as to infuse a reagent; and
a recessed portion formed in an outer circumferential surface of the tubular member and extending in an axial direction thereto such that a cross sectional shape of the tubular member perpendicular to the axial direction is a shape in which at least a portion of the outer circumference of an annular cross section has been recessed radially inward,
wherein the three lumens include:
a needle-shaped tube member lumen into which the needle-shaped tube member is inserted;
a first guide wire lumen into which a first guide wire, that is extended from a tip of the tubular member, is inserted in such a manner that the first guide wire can be moved in the axial direction of the tubular member; and
a second guide wire lumen into which a second guide wire is inserted, wherein the second guide wire is extended from the tubular member in a direction away from the first guide wire,
wherein a balloon that can expand and contract is attached to an outside portion of the tubular member; and wherein a balloon lumen for conducting fluid for expanding the balloon is provided within the tubular member,
wherein a center of the extrusion aperture is disposed on a plane that includes central axes of the needle-shaped tube member lumen and the balloon lumen.

16. The infusion device according to claim 15, wherein the needle-shaped tube member can be connected to a reagent supply device that supplies a reagent into the needle-shaped tube member.

17. The infusion device according to claim 15, wherein a maximum width of the tubular member in a direction of extrusion of the needle-shaped tube member from the extrusion aperture in a cross section of the tubular member taken perpendicular to its axis is smaller than a maximum width of the tubular member in a direction perpendicular to the direction of extrusion of the needle-shaped tube member in that cross section.

18. The infusion device according to claim 15, wherein a front end portion of the tubular member, in a direction of insertion into the body, is smaller in a cross section when taken perpendicular to the axial direction than in an area other than the front end portion of the tubular member.

19. An infusion device comprising:
a tubular member, made of a tube member that can be inserted into a body, in which at least three lumens are provided;
a needle-shaped tube member, made of a thin tube, that is inserted into any one of the three lumens within the tubular member such that the needle-shaped tube member can be moved axially, and its tip is extruded outside through an extrusion aperture provided in the tubular member so as to infuse a reagent;
convex curved corner portions formed in an outer circumference of the tubular member, which in a cross section perpendicular to an axial direction of the tubular member correspond to apexes of a triangle that is formed having center points of any three lumens of the at least three lumens as apexes; and
curved surfaces or flat surfaces formed in the outer circumference of the tubular member, which connect adjacent convex curved corner portions,
wherein the three lumens include:
a needle-shaped tube member lumen into which the needle-shaped tube member is inserted;
a first guide wire lumen into which a first guide wire, that is extended from a tip of the tubular member, is inserted in such a manner that it can be moved in the axial direction of the tubular member; and
a second guide wire lumen into which a second guide wire is inserted, wherein the second guide wire is extended from the tubular member in a direction away from the first guide wire,
wherein a plane that includes a central axis of the first guide wire lumen and a central axis of the second guide wire lumen is disposed perpendicular to a direction in which the extrusion aperture is formed.

20. The infusion device according to claim 19, wherein a maximum width of the tubular member in a direction of extrusion of the needle-shaped tube member from the extrusion aperture in a cross section of the tubular member taken perpendicular to its axial direction is smaller than a maximum width of the tubular member in a direction perpendicular to the direction of extrusion of the needle-shaped tube member in that cross section.

21. An infusion device comprising:
a tubular member, made of a tube member that can be inserted into a body, in which at least three lumens are provided;
a needle-shaped tube member, made of a thin tube, that is inserted into any one of the three lumens within the tubular member such that the needle-shaped tube member can be moved axially, and its tip is extruded outside through an extrusion aperture provided in the tubular member so as to infuse a reagent;
convex curved corner portions formed in an outer circumference of the tubular member, which in a cross section perpendicular to an axial direction of the tubular member correspond to apexes of a triangle that is formed having center points of any three lumens of the at least three lumens as apexes; and
curved surfaces or flat surfaces formed in the outer circumference of the tubular member, which connect adjacent convex curved corner portions,
wherein the three lumens include:
a needle-shaped tube member lumen into which the needle-shaped tube member is inserted;
a first guide wire lumen into which a first guide wire, that is extended from a tip of the tubular member, is inserted in such a manner that it can be moved in the axial direction of the tubular member; and a second guide wire lumen into which a second guide wire is inserted, wherein the second guide wire is extended from the tubular member in a direction away from the first guide wire, wherein the first guide wire lumen and the second guide wire lumen are disposed on respective sides of the needle-shaped tube member lumen and sandwich the needle-shaped tube member lumen therebetween, and central axes of the three lumens are disposed on a same plane.

22. The infusion device according to claim 21, wherein a maximum width of the tubular member in a direction of extrusion of the needle-shaped tube member from the extrusion aperture in a cross section of the tubular member taken perpendicular to its axis is smaller than a maximum width of the tubular member in a direction perpendicular to the direction of extrusion of the needle-shaped tube member in that cross section.

23. An infusion device comprising:

a tubular member configured to be inserted into a body, having at least three lumens extending in its axial direction and an extrusion aperture provided on a side wall of the tubular member, one of said lumens leading to the extrusion aperture; and a needle-shaped tube member, that is inserted into said one of the lumens and is movable axially, said needle-shaped tube member having a tip end being extruded outside through the extrusion aperture for infusing a reagent, wherein the three lumens includes a first guide wire lumen into which a first guide wire that is extended from a tip of the tubular member is inserted and movable axially, and a second guide wire lumen into which a second guide wire that is extended from an opening provided on a side wall in a different direction from the first guide wire is inserted and movable axially, wherein the second guide wire lumen ends at the opening, and the tubular member has a smaller cross sectional area perpendicular to the axial direction from its tip to the opening than a cross sectional area perpendicular to the axial direction from the opening toward the rear end.

24. The infusion device according to claim 23, wherein the extrusion aperture is disposed such that the needle-shaped tube member is extruded therefrom in a direction substantially or nearly perpendicular to a plane defined by the first guide wire's inserting direction and the second guide wire's extending direction.

25. The infusion device according to claim 23, wherein the extrusion aperture is disposed between the opening and the tip of the tubular member.

26. The infusion device according to claim 23, wherein the at least three lumens are three lumens at the front end portion and four lumens at a rear end portion opposite to the front end portion.

* * * * *